US006482937B1

(12) United States Patent
Baetscher et al.

(10) Patent No.: US 6,482,937 B1
(45) Date of Patent: Nov. 19, 2002

(54) PORCINE OCT-4 PROMOTER

(75) Inventors: Manfred W. Baetscher, Portland, OR (US); Donna E. Akiyoshi, Upton, MA (US); Ruth A. Kaplan, Tewsbury, MA (US)

(73) Assignee: BioTransplant, Inc., Charlestown, MA (US)

( * ) Notice: Subject to any disclaimer, the term of this patent is extended or adjusted under 35 U.S.C. 154(b) by 35 days.

(21) Appl. No.: 08/948,113

(22) Filed: Oct. 9, 1997

(51) Int. Cl.[7] .......................... C07H 21/02; C07H 21/04

(52) U.S. Cl. .................. 536/24.1; 536/23.1; 536/24.31

(58) Field of Search ................................ 435/325, 383, 435/440, 455, 320.1; 536/24.1, 24.31; 800/13, 17, 21

(56) References Cited

U.S. PATENT DOCUMENTS 5,817,789 A * 10/1998 Heartlein et al. .......... 536/23.4

FOREIGN PATENT DOCUMENTS

| | | | |
|---|---|---|---|
| WO | WO 94/24274 | 10/1994 | C12N/15/00 |
| WO | WO 95/20042 | 7/1995 | C12N/5/10 |
| WO | 2476 | 12/1995 | C12N/5/06 |

OTHER PUBLICATIONS

Thomas e.t al., Site–Directed Mutagenesis by Gene Targeting in Mouse Embryo–Derived Stem Cells, 1987, Cell, vol. 51: 503–512.*

Campbell and Wilmut. Totipotency or multipotentiality of cultured cells: Applications and progress. Theriogenology 47: 63–72, Jan. 1997.*

Gearhart, J. New potential for human embryonic stem cells. Science 282: 1061–1062, Nov. 1998.*

Iannaccone et al. Pluripotent embryonic stem cells from the rat are capable of producing chimeras. Dev. Biol. 163: 288–292, 1994.*

Shamblott et al. Derivation of pluripotent stem cells from cultured human primordial germ cells. PNAS 95: 13726–13731, Nov. 1998.*

Stice et al. Pluripotent bovine embryonic cell lines direct embryonic development following nuclear transfer. Biol. Reprod. 54: 100–110, 1996.*

Thomson et al. Embryonic stem cell lines derived from human blastocysts. Science 282: 1145–1147, Nov. 1998.*

Okazawa et al. GenBank Accession No. S58422, Jul. 1992.*

Schoorlemmer et al. GenBank Accession No. S68053, Sep. 1994.*

Abdel–Rahman et al., 1995. Hum. Reprod. Oct. 1995; 10(10): 2787–2792. Expression of transcription regulating genes in human preimplantation embryos.

McWhir et al. 1996. Nature Genetics 14: 223–226. "Selective ablation of differentiated cells permits isolation of embryonic stem cell lines from murine embryos with a non–permissive genetic background".

Minucci et al. 1996. EMBO J. 15: 888–899 "Reinoic acid–mediated down–regulation of Oct3/4 coincides with the loss of promoter occupancy".

Mountford, P. et al. Proc Natl Acad Sci USA May 1994 10:91(10):4303–4307 Dicistronic targeting constructs reporters and modifiers of mammalian gene expression.

Okazawa et al 1991 EMBO J. 10:2997–3005. "The oct3 gene, a gene for an embryonic transcription factor is controlled by a retinoic acid repressible enhancer".

Scholer et al. 1990 Nature 344: 435–439.

Takeda et al. 1992 Nucl. Acids Res. 20:4613–4620.

Tearle et al 1996 Transplantation 61:13–19.

Yeom et al. 1991. Mechanisms of Development, 35:171–179. "Structure, expression and chromosomal location of the Oct–4 gene".

Yeom et al. 1996. Development. Mar.: 122(3): 881–894. Germline regulatory element of Oct–4 specific for the totipotent cycle of embryonal cells.

Gossler, et al., "Mouse Embryonic Stem Cells and Reporter Constructs to Detect Developmentally Regulated Genes," Science, vol. 244, pp. 463–465 (Apr. 1989).

Klug, et al., "Genetically Selected Cardiomyocytes from Differentiating Embryonic Stem Cells Form Stable Intracardiac Grafts," J. Clin. Invest., vol. 98, No. 1, pp. 216–224 (Jul. 1996).

Friedrich & Soriano, "Promotor traps in embryonic stem cells: a genetic screen to identify and mutate developmental genes in mice, " Genes and Development, 5:1513–1523 (1991).

Sutherland, et al., "An upstream activator sequence regulates the murine Pkg–1 promotor and binds multiple nuclear proteins," Gene Expr. 4(4–5):265–279 (1995).

Tearle, et al., "The alpha–1,3–galactosyltransferase knockout mouse. Implication for xenotransplantation," Transplantation 61(1):13–19 (Jan. 1996).

Joyner & Skarnes, "Mouse embryonic stem cells and reporter constructs to detect developmentally regulated genes," Science, 244(4903):463–465 (Apr. 1989).

Cormack, et al., "FACS–optimized mutants of the green fluorescent protein (GFP)," Gene (1996).

(List continued on next page.)

*Primary Examiner*—Anne-Marie Baker

(74) *Attorney, Agent, or Firm*—Elliot M. Olstein; Alan J. Grant

(57) ABSTRACT

The present invention provides for a method of isolating and/or propagating porcine stem cells, more specifically pluripotential porcine embryonic stem cells. The pluripotential cells are isolated and/or propagated by the use of a selectable marker gene which is inserted into the genetic material of the cells, and which permits the survival and growth of the porcine embryonic stem cells. The selectable marker gene is inserted so as to be regulated by a control or promoter polynucleotide sequence in the embryonic stem cells, for example the promoter polynucleotide sequence being the porcine Oct-4 promoter sequence of the present invention. The invention also provides for a transgenic pig which will constitute a source of the pluripotent cells.

3 Claims, 23 Drawing Sheets

OTHER PUBLICATIONS

Kitts, "pEGFP–1 complete sequence," Unpublished. Accession No. U55761. Jun. 17, 1996.

Kitts, "Direct Submission," Submitted Apr. 17, 1996.

Takeda, et al., "Human Oct3 gene family: cDNA sequences, alternative splicing, gene organization, chromosomal localization, and expression in adult tissues," Unpublished. Accession No. Z11900. Jun. 25, 1997.

Bell, "Direct Submission," Submitted Apr. 3, 1992.

Okazawa, et al., "The oct3 gene, a gene for an embryonic transcription factor, is controlled by a retinoic acid repressible enhancer," Embo. J., 10(10), 2997–3005 (1991).

* cited by examiner

Oct4
BssHII
BamHI
EcoRI
HindIII
KpnI
2kb

FIG. 2A

```
                                    BamHI  SmaI    PstI    Eco RI
                                    ATGGATCCCCCGGGCTGCAGGAATTCCGGG

    ATGGATCCTCGAACCTGGCTAAGCTTCCAAGGGCCTCCAGGTGGGCCTGGAATCGGACCA   60
1   M  D  P  R  T  W  L  S  F  Q  G  P  P  G  G  P  G  I  G  P     -

    GGCTCAGAGGTATTGGGGATCTCCCCATGTCCGCCCGCATACGAGTTCTGCGGAGGGATG  120
21  G  S  E  V  L  G  I  S  P  C  P  P  A  Y  E  F  C  G  G  M     -

    GCATACTGTGGACCTCAGGTTGGTCTGGGCCTAGTCCCCCAAGTTGGCGTGGAGACTTTG  180
41  A  Y  C  G  P  Q  V  G  L  G  L  V  P  Q  V  G  V  E  T  L     -

                                             Clone 16
    CAGCCTGAGGGCCAGGCAGGAGCACGAGTGGAAAGCAACTCAGAGGGAACCTCCTCTGAG  240
61  Q  P  E  G  Q  A  G  A  R  V  E  S  N  S  E  G  T  S  S  E     -

    CCCTGTGCCGACCGCCCCAATGCCGTGAAGTTGGAGAAGGTGGAACCAACTCCCGAGGAG  300
81  P  C  A  D  R  P  N  A  V  K  L  E  K  V  E  P  T  P  E  E     -

                     PstI
                             Clone 1
    TCCCAGGACATGAAAGCCCTGCAGAAGGAGCTAGAACAGTTTGCCAAGCTGCTGAAGCAG  360
101 S  Q  D  M  K  A  L  Q  K  E  L  E  Q  F  A  K  L  L  K  Q     -
```

Fig. 2B

```
         ——— POU-SPECIFIC DOMAIN ———
         AAGAGGATCACCTTGGGGTACACCCAGGCCGACGTGGGGCTCACCCTGGGCGTTCTCTTT  420
121      K  R  I  T  L  G  Y  T  Q  A  D  V  G  L  T  L  G  V  L  F   -

         GGAAAGGTGTTCAGCCAGACCACCATCTGTCGCTTCGAGGCCTTGCAGCTCAGCCTTAAG  480
141      G  K  V  F  S  Q  T  T  I  C  R  F  E  A  L  Q  L  S  L  K   -

         AACATGTGTAAGCTGCGGCCCCTGCTGGAGAAGTGGGTGGAGGAAGCCGACAACAATGAG  540
161      N  M  C  K  L  R  P  L  L  E  K  W  V  E  E  A  D  N  N  E   -

         AACCTTCAGGAGATATGCAAATCGGAGACCCTGGTGCAGGCCCGGAAGAGAAAGCGAACT  600
181      N  L  Q  E  I  C  K  S  E  T  L  V  Q  A  R  K  R  K  R  T   -

         ——— POU HOMEODOMAIN ———
         AGCATTGAGAACCGTGTGAGGTGGAGTCTGGAGACCATGTTTCTGAAGTGCCCGAAGCCC  660
201      S  I  E  N  R  V  R  W  S  L  E  T  M  F  L  K  C  P  K  P   -

         TCCCTACAGCAGATCACTCACATCGCCAATCAGCTTGGGCTAGAGAAGGATGTGGTTCGA  720
221      S  L  Q  Q  I  T  H  I  A  N  Q  L  G  L  E  K  D  V  V  R   -

         GTATGGTTCTGTAACCGGCGCCAGAAGGGCAAAAGATCAAGTATTGAGTATTCCCAACGA  780
241      V  W  F  C  N  R  R  Q  K  G  K  R  S  S  I  E  Y  S  Q  R   -
```

Fig. 2C

```
      GAAGAGTATGAGGCTACAGGGACACCTTTCCCAGGGGGGGCTGTATCCTTTCCTCTGCCC  840
261   E  E  Y  E  A  T  G  T  P  F  P  G  G  A  V  S  F  P  L  P    -

      CCAGGTCCCCACTTTGGCACCCCAGGCTATGGAAGCCCCCACTTCACCACACTCTACTCA  900
281   P  G  P  H  F  G  T  P  G  Y  G  S  P  H  F  T  T  L  Y  S    -

      GTCCCTTTTCCTGAGGGCGAGGCCTTTCCCTCTGTTCCCGTCACTGCTCTGGGCTCTCCC  960
301   V  P  F  P  E  G  E  A  F  P  S  V  P  V  T  A  L  G  S  P    -

      ATGCATTCAAACTGAGGCACCAGCCCTCCCTGGGGATGCTGTGAGCCAAGGCAAGGGAGG  1020
321   M  H  S  N  *  324

      TAGACAAGAGAACCTGGAGCTTTGGGGTTAAATTCTTTTACTGAGGAGGGATTAAAAGCA  1080

      CAACAGGGGTGGGGGGTGGGATGGGGAAAGAAGCTCAGTGATGCTGTTGATCAGGAGCCT  1140

      GGCCTGTCTGTCACTCATCATTTTGTTCTTAAATAAAGACTGGGACACACAGTAAAAAAA  1200

      AAAAAAAAAACTCGAG                                              1217
                 XhoI
```

FIG. 3A

```
        10         20         30         40         50
    *    *     *    *     *    *     *    *     *    *
GAATTCGGCT TCACCAGGCT TCGGACTTCG CCTTCTCGCC CCCGCCGGGC

        60         70         80         90        100
    *    *     *    *     *    *     *    *     *    *
GGTGGAGGCG ATGGGCCGGG AGGGCGGAGC CGGGCTGGGT TGATCCTCGG

       110        120        130        140        150
    *    *     *    *     *    *     *    *     *    *
ACCTGGCTGA GCTTCCAAGG GCCTCCCGGT GGGTCAGGGA TCGGGCCGGG

       160        170        180        190        200
    *    *     *    *     *    *     *    *     *    *
GGTTGGGCCG GGCGCCGAGG TGTGGGGGCT TCCCGCGTGC CCCCCGCCCT
```

FIG. 3B

```
       210        220        230        240        250
  *     *    *     *    *     *    *     *    *     *
ATGACTTCTG CGGAGGGATG GCCTACTGCG CACCTCAGGT CGGAGTGGGG

       260        270        280        290        300
  *     *    *     *    *     *    *     *    *     *
CTGGTGCCCC AGGGCGGCCT GGAGACCCCT CAGCCCGAGG GCGAGGCGGG

       310        320        330        340
  *     *    *     *    *     *    *     *
GGCCGGGGTG GAGAGCAACT CCGAGGGGGC CTCCCCCGAG
```

FIG. 4A

```
        10         20         30         40         50
    *    *     *    *     *    *   . *    *     *    *
GGATCCTCGG ACCTGGCTGA GCTTCCAAGG GCCTCCCGGT GGGTCAGGGA

        60         70         80         90        100
    *    *     *    *     *    *     *    *     *    *
TCGGGCCGGG GGTTGGGCCG GGCGCCGAGG TGTGGGGCT TCCCGCGTGC

       110        120        130        140        150
    *    *     *    *     *    *     *    *     *    *
CCCCCGCCCT ATGACTTCTG CGGAGGGATG GCCTACTGCG CACCTCAGGT

       160        170        180        190        200
    *    *     *    *     *    *     *    *     *    *
CGGAGTGGGG CTGGTGCCCC AGGGCGGCCT GGAGACCCCT CAGCCCGAGG
```

FIG. 4B

```
       210        220        230        240        250
    *    *     *    *     *    *     *    *     *    *
GCGAGGCGGG GGCCCGGGTG GAGAGCAACT CCGAGGGGGC CTCCCCCGAG

       260        270        280        290        300
    *    *     *    *     *    *     *    *     *    *
CCCTGTGCCG CCCCCGCTGG CGCCGCGAAG CTGGACAAGG AGAAGCTGGA

       310        320        330        340        350
    *    *     *    *     *    *     *    *     *    *
GCCGAACCCC GAAGAGGCGA GTGAGCTGCC GGGAGCTGGG GGAGGCGATC

       360        370        380        390        400
    *    *     *    *     *    *     *    *     *    *
GCGCTGGCCG GGGGCGCACG CAGGGGAGGT GGTCGCCTGC CGCCCGGGCA

    *
GGAGGGG
```

Oct-4 CLONE 3
λ Left
λ right
~7Kb
~4.2Kb
Ex 4
Ex 3
Ex 2
Ex 1
SEQ ID NO:13
SEQ ID NO:13
SEQ ID NO:7
SEQ ID NO:7
SEQ ID NO:8
SEQ ID NO:7
SEQ ID NO:16
SEQ ID NO:15

Oct-4 CLONE 4

FIG. 6A

```
        10         20         30         40         50
    *    *     *    *     *    *     *    *     *    *
AGCCATGCTG GGTTGATCCT CCCACCTGGC TGTGCTTCCA AGGGCCTCCT

        60         70         80         90        100
    *    *     *    *     *    *  .  *    *     *    *
GTTGGGTCAG GGATCTGGCG GGGGGCTGCT GGACCCAGAG GTGGGGAGGC

       110        120        130        140        150
    *    *     *    *     *    *     *    *     *    *
TTCTCTCATG CCCCCCGCCC TAGGACTTCT GCGGAGGGAT GGCCTACTGT

       160        170        180        190        200
    *    *     *    *     *    *     *    *     *    *
GCACCTCAGG TCAGAGAGGG GCTGGTGCCC CAAGGCGGCC TGGAGACCCC
```

FIG. 6B

```
       210        220        230        240        250
    *    *     *    *     *    *     *    *     *    *
TCAGCCCTAG GGCCAGGCAG GAGTCGGGGT GGGGAGCAAC TCCGAGGGGG

       260        270        280        290        300
    *    *     *    *     *    *     *    *     *    *
CCTCCCTGGA GCCCTATGCC ACCCCCGTTG GCACTGCACA GCTGGACAAG

       310        320        330        340        350
    *    *     *    *     *    *     *    *     *    *
GAGAAACTAG AGCCGAATCC TGAGAAGTCC CAGGACATCA AAACGCTTCA

       360        370
    *    *     *    *     *
GAAAGACCTT CAACAATTTG CCAAGCTT
```

FIG. 8A

```
GGATCCCTAG CCTGGAAACC TCCATAAGCC GTGGGTACTG CCCTAAGAAG AAAAAAAAAG   60
TGGTTTGCTA CCCTGGTCTA GAGCAAGCCT CCATTTTCCC CAGGAGTCAT TTCAGCTGGT  120
TTTCCCTACC AAACAGCAAG GGGATGGCCG GGCTGACAGC AGCAAAGTCA CTGTCACCTC  180
TTTGCAGCCT TGCCAGGCCA GCTGCATCTG GCAGGGAGCG GCAGCTCTCA CCTGCCCTCC  240
CTGGGTCATG CTCTACAGCC AGATACTTGG CATTTGTCTT TGTGTAGGGC CTCAATATTG  300
TACTCTAATA AGGGTACATG TGGGAGTTCC CTGGTGGCTC AGCAGTTGAG GATCTGGCAT  360
TGTCACTGCT CTGGCATGGA TCTCTGCTCT GGCGCAGGTT CAATTCCTGG CCTGGGAACT  420
TCTGTACGCC GCAGGCGTGA CTGGAAAAAT ACAGGTGGGG TGGGGTGAGG AGTGTATGTG  480
GAGAGTCTGC AAACCCAGGC CTAAATTGGT TTGGGGGACT TGAAGTTTTT AGTGACTCCC  540
TACCCAAAAG AGTGGAGAAG CCAGGTCTGA TGACTTAACC CCACTTGCAG TCTGCTCTGG  600
GCCTGCAGAG ACCTGGCCTC TGCAGAAGTG AAGCTGCCTA CACTTCAGGC CTAACAGGAG  660
GGTGGGGAGG AGAGGGGAAT AGGCTCAGCC CTGCCATGCC AAGCACCCCC AGGCTGACTA  720
GGACTCCAGA CAAATTTAGC TTGTCCTTAA GGTTCTGGGT CAGACCCCAG GCAAGCACAG  780
AACTGATCTG GCTCAGATGT CTGGCTACAA GCTATCCAGG AACCCAGGCA TCCAGCCCTC  840
CCCAGCCCTC CCCAGGCTTT CCCTCTGGAA TAGGAAGGAC ACTTGCTTAA ACCAGAAACA  900
TACCATCTAG AGCAGCTATT TATGGTGATC TAAAAAACAC AGGGTGCTAT TTAGTCGGGG  960
GTGGGTGGGA AGGGAGAAGG TGTTTAGGGT CCGCGGGAAA GTCAGGGGCA CAGGGGCTCT 1020
CTGGACCACA TGGGGAGAGG GGTTTCTGGG AGGCCAGAGG GCGAGGAGCC AAGGAGCTCA 1080
```

FIG. 8B

```
GCAGTAGATT CCCTAGGCCC GCCCCTCCCC CTCCTCAGGG AGGCCGTCTT CTTGGCAGAC 1140
AGCAGATAGA TGCATGACAA AGGGGCCATG ATGGCTCTGT CCTGGGGGTT GGGGAGATGG 1200
CTAGGGAGGG GCCCCTCCTG GTCTGAAGCA CATCTTTCCA CCCCCACCAG GCCCCTTAAT 1260
CTATCTGCTT TTGGGGCAGT TAGTAGTTTA GAGTTGAAAT AGCTCCAGCC CTGCTGCCCT 1320
ATAAATCTTT CAACAGACCT ATGGGAAGTA TTGAAATGCA TGCACGCAAT TAGTCACCCC 1380
AAACGCACAG GCCGATGGGC ACTGGAAGAG ATTCAGAGGA GAAAAAGCAA AACAAAACAA 1440
CACGGACACA CAAAAACCCA ACAGACTCAA AGGACTCCTG GTGGAGCTAA CTGGTCACAG 1500
TCTGGAGGAT GCCAGCCCCT CAAGACAGAT GCCGAGCCAC TGACCCTAGC AAACAACCTC 1560
AGACCCAGCC AAGATGAAGA GGTGTCTAGG TCCGCAGAGG TCTGTGTCCC AGTCTCAGGA 1620
GTCTGGCCTC CAAACTGTAG GAAGCTCTGA TCCATGGCTT CTCTGGAGAG CCCCCCTCAC 1680
TCAGGTTCAC CTGGGGCCTT CGTTTAGGGC AAGTTGGGGG AGCAGACAGA CAAACATCAT 1740
CCCCAGCAGA CAGCCAGTCT GAAAGCTATT CTCTTGCAAA CAGAATCAAG CACTAGGCCA 1800
GCAGCCTGAG CCTCAGGACA GACCCAGAAA AATAGACCCT GTGGGAGAGC TTAGGGCAGG 1860
ATTCCTGCAC CCCCTCCCCA ATCGCAGTTC ACCCCCTTCT GCATCTTTTC GCTAGCCCCC 1920
CAAACAAAGG CCTGGACGCC TCAGTCCTCT AGAGGGGGGA CAGGATACCT AGGTCCCAGT 1980
GGGGGGCCCT GTCTGAGGCT CAGTCTTTGA GGGGATGGGG GTGTTGTTGC TGGAGCTCTT 2040
TTAGCTGCTC TGAAGGGGAT TCTGTGTGAG GGGATTGGGG CTGGGGGGTT GGGGGGCAGG 2100
AAGCTGTCCC CAGGGGAGCC ATCCAGGCCC ATTCAAGGGT TGAGCACTTG TTTAGGGTTA 2160
```

FIG. 8C

```
GAGCTGCCCC CTCTGGGGAC CAGGATTGTC CAGCCAAGGC CATTGTCCGG CCCCCTTCCC  2220
CCAGTCCCTC CCAAGCCTCT TTGAACCTGA AGTCAGATAT TTTTCTCTCC CCCCCCCTCC  2280
CTCCTTGGCT TTCCCCACCC AGGGCCTAGG GGTGGAGGCC CAGATTGGGA GGTGGGGGAG  2340
GGAGAACAGT CAACTATGGG GCTAGATATT TGGGTCCCTG AAGGGGGGCT GGGGGACAAG  2400
GAACCTGATG TGCGCGGGGA CCCACAGCGG GGGACCTGCG AGCGGGTGTC CGATTGATTC  2460
CTCTGCCTGC ACAAAGATTG GGAGACTCAG GCCCAGTCCA TCGAGCTTGA TCCCTGGAAG  2520
GGAAAATGGG GGTTCCATCC CTGGGTCTGG TGGAAGGGAG GCCCCGGAAC CCGGAAAACT  2580
GTACGGAATG GAAGCCCGTG TGGCAGTCTG CCCCTGGTGA GGGGTGGAAT CTAATAGGCT  2640
GGGCGGATGG TTGCTGGGCA TCGCAGCTTT GGGGTGCCGG AATCTGGCCA GTAATCTAGT  2700
TGGGAATGCC TAGGTTCCCG GACTGGGGGT GAGGGCAGAG AGCAGGAATT GAGGAGTAGC  2760
TCCGGCAGGA CTTAGCACAG ACACCAGACC TGTGTGAGGA CCTGAGAGGG TCGCTGGGGT  2820
CCCTTGAGGA GACAGTGCCA GGGTCTTCGA AGAGGGGTCC AACACCTGGC TCCCCGACAG  2880
CCCCAATGTG CACAGAGCAG TGGAGAGGGC CGGGCGGCCG GTTGGGAGTT GGAGGTGAAG  2940
GCCGCATGGG GGACCTGCAC CAAGGGCCTG GGGACCGCAG AGGCGCCCGG GCGGACCTCT  3000
CCGACTTTCG CCCTCCAGAC ACCACCGCCA CCAGCCAGCA AACACCCTCC GCCTCAGTTT  3060
CTCCCACCCC CACCGACCCC TCCCCCACCC ATCCAGGGGG CGGGGCCAGA GGTCAAGGCT  3120
AGTGGGTGGG ATTGGGGAGG GAGAGAGGTG TCGAGCAGTC CCCTTGGAGA GCCCTGGTTT  3180
TACTGGGCCC CCGGCTTGGG GCGCCTTCCT TCCCC                             3215
```

FIG. 9A

The Box indicated as A is the SP1/HRE domain

```
pig oct4 2701-3215   ---------- ---------- ---------- ---------- ----TGGGAA     6
huOCT4 1-499         ---------- ---------- ---------- ---------- ----------
mOCT4 1401-1950      TGCAATGGCT GTCTTGTCCT GGCCTTGGAC ATGGGCTGAA ATACTGGGTT    50

pig oct4 2701-3215   TGCCTAGGTT CCCGGACTGG GGGTGAGGGC AGAGAGCCAG GAAT--TGAG    53
huOCT4 1-499         -------GAAT TCAAGACC-A GCCTG-GGTA ACATAGCAAG GCCCCATCTC    42
mOCT4 1401-1950      CACCCATA-T CTAGGACTCT AGACG-GGTG GGTAAGCAA- GAAC--TGAG    95

pig oct4 2701-3215   GAGTAGCTCC GGCAGGACT- -TA--GCACA -G-ACACCAG ACCTGT-GT-    95
huOCT4 1-499         TACTAAAAAT AAAAAAACTA ACAGGGCACA -GTGGTCCAA GCCTGTAGTC    91
mOCT4 1401-1950      GAGTGGCCCC AGAAA---TA AT-TGGCACA CGAACATTCA A-TGGATGTT   140

pig oct4 2701-3215   -GAG-GACCT GAGAGG--GT CGCTG--GGG TCCCTTGAGG AGACAGT-GC   138
huOCT4 1-499         CCAGCCACTT AGGAGGCTGG AGCAGAAGGA TTGCTT-TGG -CCCAGTAGA   139
mOCT4 1401-1950      TTAGGCTCTC CAGAGGATG- -GCTGAGTGG GC-TGTAAGG A--CAG--GC   183
```

FIG. 9B

```
pig oct4 2701-3215   C-AGGGTCTT CGAAGAGGGG TCCAACA--C CTGGCTCCCC GACAGCCCCA   185
huOCT4 1-499         T-CGAGGCTA CATTGAG--- -CCATCA--T TGTACTCCAC TGCA-CTCCA   181
mOCT4 1401-1950      CGAGAGGCTG C----AGTG- -CCAACAGGC TTTGTGGTGC GATGGGGC--   225

pig oct4 2701-3215   ATGTGCACAG AGCAGTGGAG AGG-GCCGGG CGGCCGGTTG GGAGTTGGAG   234
huOCT4 1-499         GTCTGGGCAA CAAAGT-GAG A---CCCTGT C--TTAAAAA ATAAAAATAA   225
mOCT4 1401-1950      ATCCGAGCAA CTGGTTTGTG AGGTGTCCGG TGACCCA-AG GCAGGGGTGA   274

pig oct4 2701-3215   GTGAAGGCCG CATGGGGGAC CTGCACCAAG GGCCTGGGGA CCGCAGAGGC   284
huOCT4 1-499         AAAAAGTTTC TGTGGGGGAC CTGCACTGAG GTCCTGG--- -----AGGGC   268
mOCT4 1401-1950      GAGGACCTTG AAGGTTGAAA ATG-AAGGCC TTCCTGGGGT CC-------C   316

pig oct4 2701-3215   GCCCGGGCGG ACCTCTCCGA CTTTCGCCCT C--CAGACAC CACCGCCACC   332
huOCT4 1-499         GCC-AGTTGT GTCTC-CCGG TTTTCCCCTT CCACAGACAC CATTGCCACC   316
mOCT4 1401-1950      GTCC-TAAGG GT-TGTCCTG -TCCAGACCT CCCCA---AC CTCCGTCTGG   360

pig oct4 2701-3215   AGC---CA-G CAAACAC-CC TCCGCCTCAG TTTCTCCCAC CCCCACCGAC   377
huOCT4 1-499         ACCAT-TAGG CAAACATGCC TTCGCCTCAG TTTCTCCC-- -CCCACCTCC   362
mOCT4 1401-1950      AAGACACAGG CAGATA-GCG CTCGCCTCAG TTTCTCCACC CCC-ACAGCT   408
```

FIG. 9C

```
                                                                            A
pig oct4 2701-3215   CC-CTCCCCC ACCCATCCAG GGGGCGGGGC CAGAGGTCAA GGCTAGTGGG   426
huOCT4 1-499         CT-CTCCTCC ACCCATCCAG GGGGCGGGGC CAGAGGTCAA GGCTAGTGGG   411
mOCT4 1401-1950      CTGCTCCTCC ACCCACCCAG GGGGCGGGGC CAGAGGTCAA GGCTAGAGGG   458

pig oct4 2701-3215   TGGGATTGGG GAGGGAGAGA GGTGTCGAGC AGTCCCCTTG GAGAGCCCTG   476
huOCT4 1-499         TGGGACTGGG GAGGGAGAGA GGGGTTGAGT AGTCCCTTCG CA-AGCCCTC   460
mOCT4 1401-1950      TGGGATTGGG GAGGGAGAG- ---GTGAAAC CGTCCC-TAG GTGAGCCGTC   503

pig oct4 2701-3215   GTTTTACTGG GCCCCCGGCT TGGGGCGCCT TCCTTCCCC- -------      515
huOCT4 1-499         ATTTCACCAG GCCCCCGGCT TGGGGCGCCT TCCTTCCCC- -------      499
mOCT4 1401-1950      TTTCCACCAG GCCCCCGGCT CGGGGTGCCC ACCTTCCCCA TGGCTGG      550
```

FIG. 10A

```
Pig Oct-4 promoter   TCACAGTCTG GAGGATGCCA GCCCCTCAAG ACAGATGCCG AGCCACTGAC   1544
Mus S58422S1         ---------- ---------- ---------- ---------G AGCCACTGAC    440

Pig Oct-4 promoter   CCTAGCAAAC AACCTCAGAC CCAGCCAAGA TGAAGAGGTG TCTAGGTCCG   1594
Mus S58422S1         CCTAGCCAAC A-GCTCAG-- ---GC---G- -G--GCTGGG CCCAGG--CT    475

Pig Oct-4 promoter   CAGAGGTCTG TGTCCCAGTC TCAGGAGTCT GGCCTCCAAA CTGTAGGAAG   1644
Mus S58422S1         CAGAACTCTG T---CCTGGC T----A---T G-----TACA CTGTGGGGTG    510

Pig Oct-4 promoter   CTCTGATCCA TGGCTTCTCT GGAGAGCCCC CCTCACTCAG GTTCACCTGG   1694
Mus S58422S1         CTCTG----- -GGCTT-TTT ---GAGCCTG TGTTCATTCA- ---C-CCTGG    545

Pig Oct-4 promoter   GGCCTTCGTT TAGGGCAAGT TGGGGGAGCA GACAGACAAA CATCATCCCC   1744
Mus S58422S1         GGCCTTCGTT CAGGGCATGG TGTAGGAGCA GACAGACAAA CACCATCCCT    595

Pig Oct-4 promoter   AGCAGACAGC CAGTCTGAAA GCTATTCTCT TGCAAACAGA ATCAAGCACT   1794
Mus S58422S1         TGCAGACAGG CACTCTGAGG GCTATTCTCT TGCAAAGATA ACTAAGCACC    645
```

FIG. 10B

```
Pig Oct-4 promoter   AGGCCAGCAG CCTGAGCCTC AGGACAGACC CAGAAAAATA GACCCTGTGG   1844
Mus S58422S1         AGGCCAGTAA TGGGATCCTC AGACTGGGCC CAGAAAACCA ----CTCTAG    691

Pig Oct-4 promoter   GAGAGCTTAG GGCAGGATTC CTGCACCCCC TCCCCAATCG CAGTTCACCC   1894
Mus S58422S1         GAAAGTTCAG GGTAGGCTCT CTGCACCCCC TCC----TCC TAATCCCGTC    737

Pig Oct-4 promoter   CCTTCTGCAT CTTTTCGCTA GCCCCCCAAA CAAAGGCCTG GACGCCTCAG   1944
Mus S58422S1         TCCTTAGTCT CTTTCCGCCA GCAC----AG CAATGG--CG GACGGCTGCG    781

Pig Oct-4 promoter   TCCTCTAGAG GGGGCACAGG A-TACCT--A GG--TCCCAG T-GGGGGGCC   1988
Mus S58422S1         T-GACCAGGA TGAACACCGG ACTCCCTGCA GGAAGGGAAG CAGGGTATCT    830

Pig Oct-4 promoter   CTGTCTGAGG CTCAGTCTTT GAGGCGATGG GGGTGTTGTT GCTGGAGCTC   2038
Mus S58422S1         CCATCTGAGG CTCTGTCTTT GAGGAGA--- -GG------- --TGGAG---    864

Pig Oct-4 promoter   TTTTAGCTGC TCTGAAGGGG ATTCTGTGTG AGGGGATTGG GGCT---G-G   2084
Mus S58422S1         ----AGCTG- -GGGAAG--- -TCTTGTGTG AGGGGATTGG GGCTCAGGAG    904

Pig Oct-4 promoter   GGGGTTGGGG CGCAGGAAGC TGTCCCCAGG GGAGCCATCC AGGCCCATTC   2134
Mus S58422S1         GGGGTTGGGG AGCAGGAAGT TGTCCCCAGG GGAGCCATCC TGGCCCATTC    954
```

FIG. 10C

```
Pig Oct-4 promoter   AAGGGTTGAG CACTTGTTTA GGGTTAGAGC TGCCCCCTCT GGGGACCAGG   2184
Mus S58422S1         AAGGGTTGAG TACTTGTTTA GGGTTAGAGC TGCCCC-TCT GGGGACCAGG   1003

Pig Oct-4 promoter   ATTGTCCAGC CAAGGCCATT GTCCGGCCCC CTTCCCCCAG TCCCTCCCAA   2234
Mus S58422S1         ATTGTCCAGC CAAGGCCATT GTCCTGCCCC CTTCCCCCAG TCCCTCCCAG   1053

Pig Oct-4 promoter   GCCTCTTTGA ACCTGAAGTC AGATATTTT-T TCTCTCCCCC CCCCTCCC-T   2282
Mus S58422S1         GCCCCTTTGA ACCTGAAGTC AGATATTTTCT TCTCTCTACC CACCTCCCAC   1103

Pig Oct-4 promoter   CC-TTGGCTT TCCCACCCA GGGCTAGGG GTGGAGGCCC AGATTGGGAG   2331
Mus S58422S1         CCGTTGGCTT TCTCCACCCA GGAACTAGG- CTGGAAGCTG GGATGAGGAG   1152

Pig Oct-4 promoter   GTGGGGGAGG GAGAACAGTC AACTATGGGG CTAGATATTT GGGTCCCTGA   2381
Mus S58422S1         GTGGGGGAGG GAGAAC---- ---------- ---------- ----------   1168
```

PORCINE OCT-4 PROMOTER

BACKGROUND OF THE INVENTION

This invention relates to a method of isolating and/or enriching and/or selectively propagating pluripotential porcine cells, genetically modified porcine cells and pigs for use in said method, transgenic pigs providing a source of such cells and genetic selectable marker constructs for producing genetically modified cells and transgenic pigs.

Stem cells are progenitor cells which have the capacity both to self-renew and to differentiate into mature somatic cells. Embryonic stem cells are the archetypal stem cell, being capable of differentiating to form the whole gamut of cell types found in an adult animal. Such stem cells are described as "totipotential" or "pluripotential" as they are capable of differentiating into many cell types. Other types of stem cells, for example bone marrow stem cells and epidermal stem cells, persist in the adult animal. These stem cells have a more restricted capacity for differentiation.

In general, when required for research purposes or for medical use, stem cells have to be isolated from tissue samples by various fractionation procedures. However, even after careful segregation of cell types these stem cell preparations consist of mixed cell types, and while enriched for stem cells include high proportions of differentiated cells which are not categorized as stem cells.

Furthermore, most stem cells cannot be grown readily in culture. When attempts are made to culture stem cells, the cells being cultured (which ordinarily contain a mixed population of cell types) grow at different rates and stem cells rapidly become overgrown by non-stem cell types. An exception is that embryonic stem cells from two specific strains of mice (129 and Black 6) can be cultured in vitro (Evans et al. (1981) Nature 292:154–156). Thus, established lines of murine embryonic stem cells can be obtained by culturing early (3½ day) embryonic cells from murine strain 129 and Black 6, or hybrids thereof. Embryonic cell lines from species other than the mouse are not so easily propagated. For an extensive review of isolation and propagation of stem cells see PCT publication WO 94/24274, incorporated by reference herein.

There has developed a pressing need to isolate and maintain in vitro embryonic stem cells from species of animals other than murine, such as other laboratory animals and domesticated animals, and most especially, from pigs. However, prior to the present invention the problems associated with producing cultures of porcine (or pig) stem cells, including the problem of producing cell populations of a satisfactorily low degree of heterogeneity and the problem of overgrowth in culture of non-pluripotent porcine cells, have not been solved. A particular problem associated with the continuing presence of certain differentiated cell types is that these can cause elimination of stem cells from the culture by inducing their differentiation or programmed cell death.

Thus according to the present invention, there is provided a porcine cell capable of being cultured under appropriate selective culture conditions so as to enable selective propagation of pluripotential stem cells, characterized in that said pluripotent porcine cells contain a genetic selectable marker, whereby a gene product associated with the genetic selectable marker is produced and which under said culture conditions causes selective survival and/or division of the desired pluripotent cells to occur. "Selective culture conditions" are those conditions under which a population of cells is selectively grown. For example, to selectively grow cells that contain a gene which transfers resistance to a specific drug, the selective culture conditions would contain the drug so that all cells that did not express the drug resistance would be eliminated. Such selective culture conditions are well known in the art.

The invention further provides according to another aspect thereof, a transgenic animal, in this instance a transgenic pig, having genetic characteristics such that it or its progeny, during embryonic development or later life, constitute a source of porcine pluripotential cells as defined above. Such transgenic pigs may be produced according to the invention by introducing a genetic selectable marker into a fertilized oocyte or an embryonic cell, the genetic marker having the characteristics defined below, and utilizing the resulting transformed oocyte or embryonic cells as a progenitor cell for the desired transgenic animal.

A further aspect of the invention is vectors for use in producing an animal cell, for example a pig cell. Thus the invention further provides vectors for use in genetically modifying animal cells so as to produce transformed cells suitable for use as the source of cells for the method referred to below, said vector comprising a first genetic component corresponding to a genetic selectable marker and a second genetic component which, in the genetically modified porcine cell(s), results in the differential expression of the genetic selectable marker as a stably integrated construct. Such vectors may be in the form of expression vectors in which said second genetic component includes control sequences which are differentially activated in pluripotential stem cells and in cells other than the desired stem cells. The invention covers vectors which when used to transform porcine stem cells become integrated into the animal genome as well as vectors which do not become so integrated.

SUMMARY OF THE INVENTION

The present invention provides for a method of isolating and/or propagating porcine stem cells, more specifically pluripotential porcine embryonic stem cells. The pluripotential (or "pluripotent") cells are isolated and/or propagated by the use of a selectable marker gene or nucleic acid sequence which is inserted into the genetic material of cells contained in a cell culture comprising porcine pluripotent embryonic stem cells, and which permits the survival and growth of said porcine embryonic stem cells. The selectable marker gene or nucleic acid sequence is inserted so as to be regulated by a control or promoter nucleotide sequence in said embryonic stem cells, for example the control sequence being the porcine Oct-4 promoter nucleotide sequence as described below. The terms "Oct-4 promoter nucleotide sequence" or "Oct-4 promoter sequence" refer to the promoter region of the Oct-4 gene, or any fragment of the promoter region that maintains promoter activity. The invention also provides for a transgenic pig which will constitute a source of said pluripotent cells.

By providing a sufficient and reliable source of porcine pluripotential embryonic stem cells, the present invention permits those skilled in the art to genetically modify the cells with a desired genetic modification. For example, said embryonic stem cells may be genetically altered so as to not express a cell surface membrane protein that may cause rejection of porcine cells after xenotransplantation. Said genetically altered cells are then useful in creating a transgenic pig, or line of transgenic pigs, which will not express said surface membrane protein and which, therefore, will contain organs that are less likely to be rejected upon xenotransplantation.

BRIEF DESCRIPTION OF THE FIGURES

FIG. 1A shows a restriction map of an Oct-4 cosmid derived from the tw5g complete t-haplotype. The position of the transcription unit is indicated with a horizontal arrow running 5' to 3'. The position of the BamHI site missing in wild-type (C3H) and responsible for the restriction fragment length polymorphism (RFLP) between t and wild-type is marked with an asterisk. A vertical arrow indicates a BssHII site; NotI, Nrul and MluI sites were absent. FIG. 1B shows the exon/intron organization of the Oct-4 transcription unit.

FIGS. 2A, 2B, and 2C collectively show the polynucleotide sequence of F9 murine Oct-4 cDNA (SEQ ID NO: 33), and the deduced amino acid sequence (SEQ ID NO: 34), of murine Oct-4 protein. The numbering (right for the nucleic acid sequence; left for the amino acid sequence) begins at the putative initiation codon. The POU-specific domain and the POU-homeodomain are marked above the nucleotide sequence.

FIGS. 3A and 3B collectively show the polynucleotide sequence of a portion of porcine Oct-4 exon 1 (SEQ ID NO: 6) determined from genomic porcine DNA obtained from a commercial source (Clontech).

FIGS. 4A and 4B collectively show the polynucleotide sequence of a contiguous portion of porcine Oct-4 exon 1 (SEQ ID NO: 11) determined from genomic porcine DNA from d/d haplotype miniswine.

FIGS. 6A and 6B collectively show the polynucleotide sequence of the porcine Oct-4-related sequence (SEQ ID NO: 32) derived from Lambda clone #4.

FIGS. 8A, 8B, and 8C collectively show the promoter polynucleotide sequence (SEQ ID NO: 24) for approximately 3 Kb 5' to the translation initiation codon for porcine Oct-4.

FIGS. 9A, 9B, and 9C collectively show an alignment comparison of the human, mouse and porcine Oct-4 promoter polynucleotide sequences. The sequence for the human Oct-4 promoter region includes nucleotides 1–499 from Genbank Accession Number Z11900 (SEQ ID NO: 35); the sequence for the mouse Oct-4 promoter region includes nucleotides 1401–1950 from Genbank Accession Number S58422S1 (SEQ ID NO: 36); the sequence for the porcine Oct-4 promoter region includes nucleotides 2701–3215 from SEQ ID NO:24. The major capping sites (RNA initiation sites) for the murine sequence (Okazawa et al. (1991) EMBO J. 10:2997-3005) are at nucleotides 480 and 501. The box marked as "A" is the SP1/HRE domain.

FIGS. 10A, 10B, and 10C collectively show an alignment comparison of the Retinoic Acid Responsive Element (RARE) regions of the pig and mouse Oct-4 promoter regions. The mouse sequence also shows high sequence identity within the region corresponding to S584221S1 nucleotides 430 through 1168 (SEQ ID NO: 37) and porcine Oct-4 promoter sequence nucleotides 1534 through 2347 (with residues 1495 through 2381 of SEQ ID NO: 24 being shown). This region includes the retinoic acid responsive element located between nucleotides −1132 through −889 of Okazawa et al. (supra) (corresponding to nucleotides 609 through 1101 of Genbank Accession Number S584221S1). This region is also known as the "proximal enhancer region".

DETAILED DESCRIPTION OF THE INVENTION

Figure 1A:
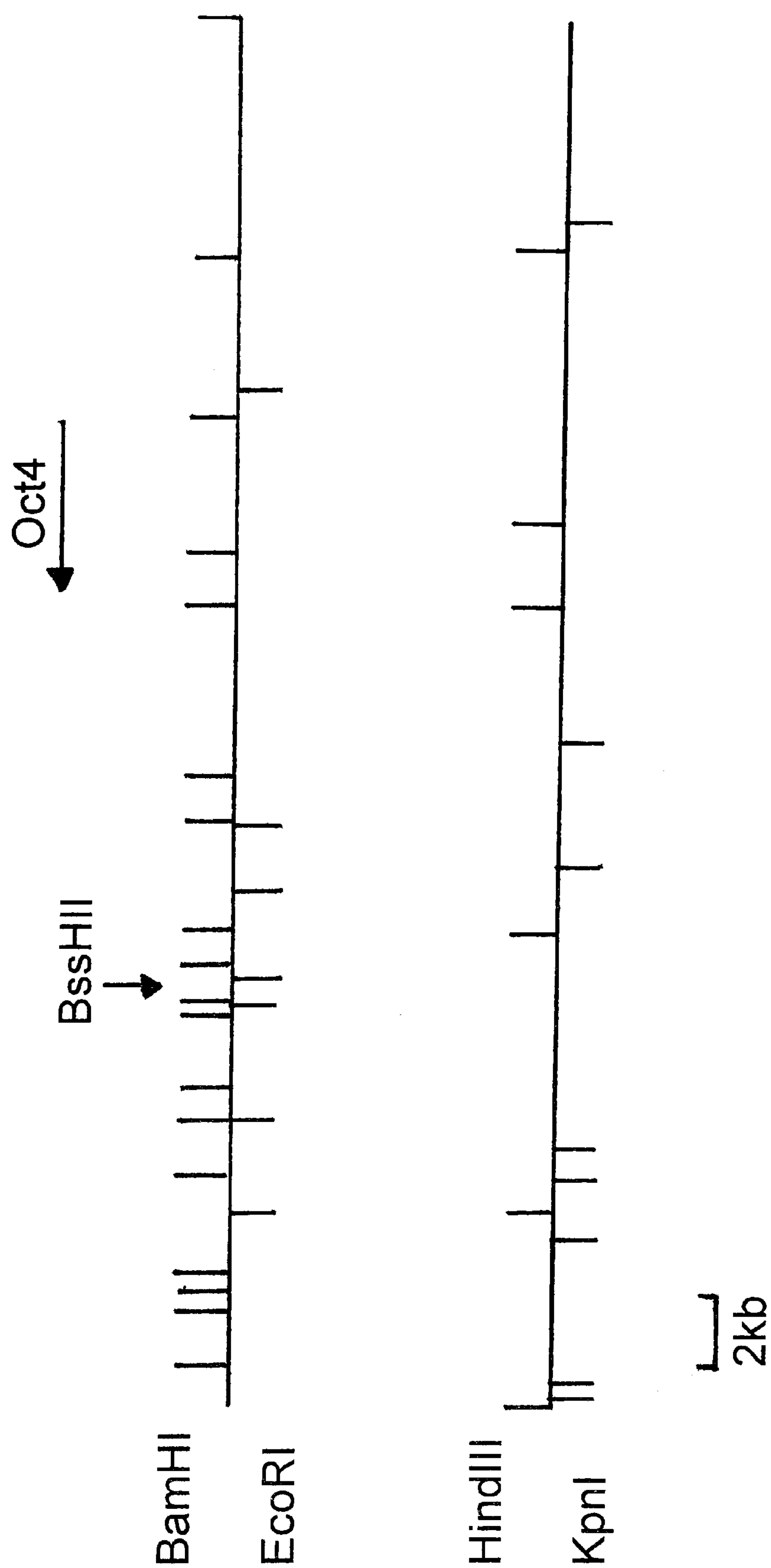
FIGS. 1A and 1B represent the genomic structure of murine Oct-4 (Yeom et al. (1991) Mechanisms of Development 35:171–179).

There is an ever growing need for a sufficient and reliable source of pluripotential porcine embryonic stem cells. A particular desire for porcine embryonic stem cells is grounded in the need to be able to genetically modify the stem cells so that later cell development will result in an animal (pig) which will contain organs capable of being accepted immunologically by a recipient host. Once one is able to culture a large number of porcine stem cells and expand them in that state, then they can more easily be genetically modified to create a line of cells which will mature into organs less likely to be rejected after transplantation. These cells can, according to the invention, be implanted to create a transgenic pig (and a pig line) which will contain organs useful for transplantation into a host.

Donor organ shortages have led to hopes that xenotransplantation could serve as an alternative means of organ availability. Swine, particularly miniswine, are an attractive alternative to nonhuman primate donors because of potentially greater availability, the reduced risk of zoonotic infections, appropriate size of organs and the reduced social and ethical concerns. However, one of the major barriers to xenotransplantation is hyperacute rejection. This phenomenon describes a very rapid and severe humoral rejection, which leads to destruction of the graft within minutes or hours of the transplant of the donor organ. Hyperacute rejection is apparently mediated by a complex series of events, including activation of the complement systems, activation of blood coagulation proteins, activation of endothelial cells and release of inflammatory proteins.

The hyperacute rejection process is initiated when the natural antibodies of the recipient bind to cells of the donor organ. The major cell surface protein (or epitope) that is recognized on porcine cells by human antibodies is the Galα1, 3Gal β1,4GlcNAc structure. This structure is expressed at high levels on all mammalian cells, including swine cells, with the exception of human and old world non-human primates. A specific transferase, namely α1,3 galactosyltransferase, is responsible for the transfer of a terminal galactose to the terminal galactose residue of N-acetyllactosamine-type carbohydrate chains and lactosaminoglycans. If one could eliminate or prevent the expression of the Galα1,3Gal β1,4GlcNAc epitope from the surface of the porcine cells in a transgenic pig, the cells would less likely be rejected by human antibodies and thus organs from such a transgenic pig would more likely be accepted upon transplantation.

In order to eliminate the α1,3 galactosyltransferase activity in the pig, it would be highly desirable to have an abundant source of porcine embryonic stem cells, in order that sufficient genetic manipulations of the cells could be performed successfully. Using cultured porcine embryonic stem cells, a mutation, preferably a null mutation, is introduced by gene targeting at the native genomic locus encoding α1,3 galactosyltransferase. In order to permit such genetic manipulations in a desired quantity, porcine embryonic stem cells must be propagated in large amounts. Once the genetic manipulation is achieved (i.e., the α1,3 galactosyltransferase activity is eliminated), the stem cells may be utilized in making a line of transgenic pigs. Such transgenic pigs would contain the genetically manipulated cells, which would not express the α1,3 galactosyltransferase activity, and would therefore provide a supply of organs available for xenotransplantation with a minimized risk of rejection.

The isolation of embryonic stem cells from pigs would provide a method for the multiplication of animals with desired characteristics, an efficient means of producing transgenic animals, and a valuable model for studying cell development and differentiation. One of the major problems associated with the derivation of embryonic stem cells is that most stem cells cannot be grown readily in culture and when attempts are made to culture stem cells, the cells being cultured (usually a heterogeneous cell type population) grow at different rates and stem cells rapidly become overgrown by non-stem cell types. The present invention provides a method for isolating and/or enriching and/or selectively propagating pluripotential porcine embryonic cells which comprises maintaining a source of said cells under culture conditions conducive to cell survival, characterized in that the source of cells includes cells containing a genetic selectable marker which is is operatively linked to a porcine promoter nucleotide sequence which provides differential expression of the selectable marker in embryonic stem (pluripotential) cells and cells other than the desired stem cells, whereby differential expression of said genetic selectable marker results in preferential survival and/or division of the desired pluripotential porcine cells. Cell cultures and culture conditions suitable for propagating cells of the present invention are known by those skilled in the art. Suitable cell cultures may be, for example, found in Wurst, W. and A. L. Joyner, "Production of Targeted Embryonic Stem Cell Clones", in Gene Targeting: A Practical Approach (Ed. A. L. Joyner) 1993, Oxford Univ. Press; and Hashimoto et al., WO 95/34636.

In carrying out the method of the invention, the source of cells may include pluripotential cells containing a positive selectable marker and expression of the marker is used to permit isolation and maintenance of the pluripotential cells. Alternatively (or additionally), the source of cells may include a negative selectable marker which is expressed in cells other than the desired pluripotential cells and is used to deplete the source of cells other than the desired pluripotential cells. The genetic selectable marker may, for example, be a foreign gene, a cellular gene or an antibiotic resistance gene such as for example the bacterial neomycin resistance gene.

It is preferred that the genetic selectable marker is operatively linked to a promoter nucleotide sequence which is differentially active in pluripotential stem cells and non-pluripotential cells. Promoter sequences may be included in the expression construct prior to introduction into the cells. The genetic selectable marker may be introduced into the source of cells by a variety of means known in the art including, but not limited to, injection, transfection, electroporation or by infection with a viral vector.

Further, the source of cells may be produced by transfection extemporaneously, or the source of cells may be derived from a transgenic animal, e.g., the founder transgenic animal or an animal at least one ancestor of which has had the aforementioned genetic marker introduced into its genetic complement. In such transgenic animals it is possible for the genetic selectable marker to pass down the germ line eventually resulting in the production of progeny, from the tissues of which the required source of cells can be derived.

A wide variety of known gene products may be relied upon for selective isolation and propagation of the desired porcine stem cells, including genetic selectable markers which are designed to protect the desired cells from the effects of an inhibiting factor present in the culture medium. In this instance, the inhibiting factor can, for example, be an antibiotic substance which inhibits growth or reproduction of cultured cells not expressing the gene (i.e., cells other than the desired pluripotential stem cells). Alternatively, the genetic selectable marker may selectively permit the growth of pluripotential stem cells using a marker known in the art. In this instance the marker may encode a growth factor, a growth factor receptor, a transcription factor, or an immortalizing factor. Alternatively, the selectable marker may be a cell surface antigen or other gene product which allows purification or depletion of expressing cells for example by panning or fluorescence-activated cell sorting (FACS). The invention thus enables porcine stem cell populations to be obtained and/or maintained having a satisfactory degree of homology. Examples of all types of selectable markers discussed above are known in the art.

The present invention permits the development of expression constructs which direct specific expression of genetic selectable markers in porcine stem cells and not in differentiated cell types. Having introduced an expression construct by transfection or via the generation of transgenic animals, stem cells present within mixed cell populations can be isolated by culturing in the presence of the selection agent in vitro, or by otherwise manipulating the culture conditions by methods well known in the art.

One example of a gene which displays a suitably restricted stem cell expression pattern, and therefore should provide a suitable promoter polynucleotide sequence for use in controlling stem cell specific regulatory elements for the expression of a genetic selectable marker in accordance with the invention, is the Oct-4 gene. Octamer binding transcription factor 4 (hereinafter "Oct-4") is a member of the POU family of transcription factors. Oct-4 transcription, controlled by the Oct-4 promoter polynucleotide sequence, is activated between the 4 and 8-cell stage in the developing embryo and it is highly expressed in the expanding blastocyst and then in the pluripotent cells of the egg cylinder. Transcription is down-regulated as the primitive ectoderm differentiates to form mesoderm and by 8.5 days post coitum is restricted to migrating primordial germ cells. High level Oct-4 gene expression is also observed in pluripotent embryo carcinoma and embryonic stem cell lines and is down-regulated when these cells are induced to differentiate. As a result of the inventors' discovery of the sequence of the porcine Oct-4 promoter polynucleotide sequence, it is now possible to link the porcine Oct-4 promoter polyncleotide sequence to a genetic selectable marker in porcine cells and thus isolate and/or propagate a large number of porcine pluripotent stem cells.

As described herein, Applicants' Oct-4 promoter polynucleotide sequence is useful to control a genetic selectable marker sequence to permit propagation of large amounts of porcine embryonic stem cells. The Oct-4 promoter polynucleotide sequence may be used in its entirety, or a portion or fragment of the promoter sequence may be used in which the portion maintains the promoter activity. One skilled in the art would easily be capable of, using Applicants' sequence, joining a selectable marker to a portion or fragment of the porcine Oct-4 promoter polynucleotide sequence, transfecting the Oct-4-marker construct into a colony of cells, and growing the transfected cells in the appropriate medium to determine if the genetic selectable marker is translated. Within the scope of Applicants' invention are such portions or fragments that retain promoter activity, such portions having preferably at least 90% sequence identity, more preferably 95% sequence identity, and most preferably 98% sequence identity to the porcine Oct-4 promoter polynucleotide sequence as shown in FIG. 8 or a portion of said Oct-4 promoter polynucleotide sequence, wherein said portion preferably consists of contiguous nucleotides from the porcine Oct-4 promoter polynucleotide sequence, i.e., a contiguous portion, and wherein said portion preferably comprises at least 38 nucleotides, more preferably at least 100 nucleotides, more preferably at least 200 nucleotides, more preferably at least 500 nucleotides, more preferably at least 1000 nucleotides, more preferably at least 1500 nucleotides, more preferably at least 2000 nucleotides, and most preferably at least 2500 nucleotides of the porcine Oct-4 promoter polynucleotide sequence shown in FIG. 8.

Also within the scope of Applicants invention are polynucleotide sequences which hybridize to all or a portion of the Oct-4 promoter polynucleotide sequence as shown in FIG. 8. Preferred under the scope of Applicants' invention are polynucleotide sequences which hybridize under high stringency conditions to all or a portion of the porcine Oct-4 promoter polynucleotide sequence as shown in FIG. 8. Conditions under which hyridization will occur are known in the art and can be found in, for example, Bulletin 1234, Bio-Rad Laboratories, incorporated by reference herein.

The polynucleotides of the present invention may be in the form of DNA which DNA includes genomic DNA and synthetic DNA. The DNA may be double-stranded or single-stranded, and if single stranded may be either of the strands which together comprise the promoter. Such sequences are useful either in the promoter functionality or as probes to retrieve the promoter sequences.

Fragments of the full-length promoter of the present invention may be used as hybridization probes for the DNA containing the promoter or to isolate other DNAs which have a high polynucleode sequence identity to the promoter. Probes of this type preferably have at least 10 nucleotides, preferably at least 15 nucleotides, and even more preferably at least 30 nucleotides and may contain, for example, at least 50 or more nucleotides. In fact, probes of this type having at least up to 150 nucleotides or greater may be utilized. An example of a screen comprises isolating the promoter region of the porcine Oct-4 gene by using the known DNA sequence to synthesize an oligonucleotide probe. Labeled oligonucleotides, having a sequence complementary to that of the promoter or portion of the promoter sequences of the present invention are used to identify those polynucleotides that hybridize to, in a complementary sense, the promoter fragment, and have an identity as described above.

It is also appreciated that such probes can be and are preferably labeled with an analytically detectable reagent to facilitate identification of the probe. Useful reagents include but are not limited to radioactive labels, fluorescent dyes or enzymes capable of catalyzing the formation of a detectable product. The probes are thus useful to isolate complementary copies of the Oct-4 related promoter sequences from other sources or to screen such sources for related sequences.

The present invention further relates to polynucleotides which hybridize to the hereinabove-described sequences (SEQ ID NO:24 or a polynucleotide sequence encoding the same promoter as encoded by the sequence according to SEQ ID NO:24) if there is at least 70%, preferably at least 90%, and more preferably at least 95% identity between the sequences.

The polynucleotides of the present invention are preferably provided is an isolated form, and preferably are purified to homogeneity.

The term "isolated" means that the material is removed from its original environment (e.g., the natural environment)

Moreover, within the scope of Applicants' invention is the use of the porcine Oct-4 promoter polynucleotide sequence, or a portion thereof, connected to all or a portion of exon 1 and intron 1 of the porcine Oct-4 gene. The Oct-4 promoter plus exon/intron 1 is then joined to a genetic selectable marker according to the invention to be used in selectively propagating porcine stem cells.

Using applicants' teaching, pluripotential porcine embryonic stem cells are created in which the porcine Oct-4 promoter polynucleotide sequence is employed to drive stem cell specific transcription of a selectable marker. The stem cells are propagated in large quantities and are available for further genetic manipulation (e.g., to eliminate the $\alpha$1,3 galactosyltransferase activity). Applicants' invention also provides for transgenic pigs in which a porcine Oct-4 promoter polynucleotide sequence drives specific transcription of the selectable marker. An appropriate genetic selectable marker, for example, is the neomycin phosphotransferase gene which confers resistance to the antibiotic G418, although other genetic selectable markers are known and are available to those skilled in the art.

Selectable marker genes under the control of the porcine Oct-4 promoter may, according to the invention, be applied to the isolation of embryonic stem cell lineages from a transgenic pig.

Accordingly, this invention includes the generation of transgenic pigs which express the porcine Oct-4 promoter polynucleotide sequence linked to a genetic selectable marker, for example the selectable marker being $\beta$-geo (sequences encoding a fusion protein of $\beta$-galactosidase and neomycin phosphotransferase II). The $\beta$-galactosidase activity enables visualization of cells expressing the marker and the neomycin phosphotransferase activity confers resistance to the antibiotic G418. Embryonic stem cells are then isolated from the transgenic pigs using culture conditions to support the growth of undifferentiated cells and maintaining selective pressure for cell expressing $\beta$-geo under the control of the Oct-4 promoter polynucleotide sequence.

Also included within the scope of the invention are transgenic pigs which contain cells expressing a genetic selectable marker under the control of the porcine Oct-4 promoter polynucleotide sequence according to the present invention, as well as transgenic pigs which contain cells expressing a genetic selectable marker under the control of the porcine Oct-4 promoter polynucleotide sequence which have been genetically manipulated to eliminate the $\alpha$1,3 galactosyltransferase activity. The pigs containing the genetically manipulated cells are good resources for organs suitable for transplantation because of the minimal risk of hyperacute rejection.

Figure 1B:
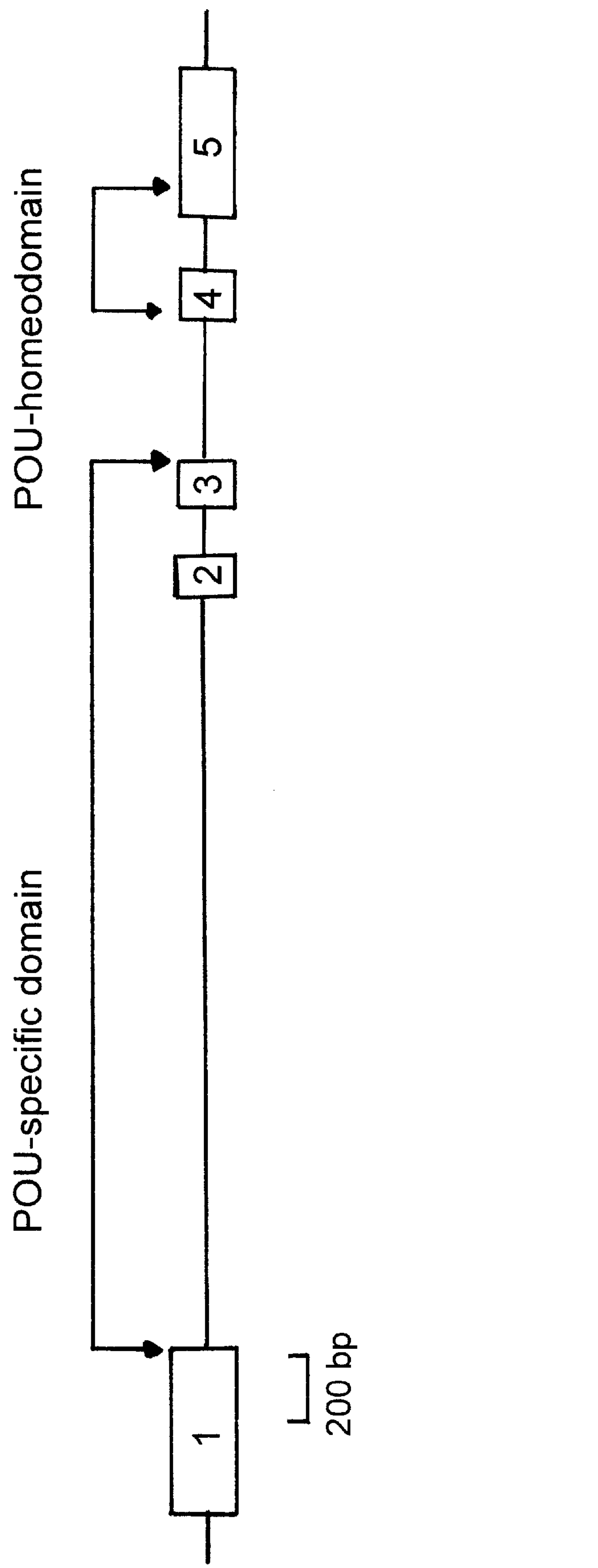

In order to obtain the porcine Oct-4 promoter polynucleotide sequence, Applicants isolated porcine Oct-4 gene sequences and used those sequences to isolate and determine the DNA sequence upstream of the start of transcription initiation. The genomic map of the mouse Oct-4 gene (Yeom et al. (1991) Mechanisms of Development 35:171–179) is presented in FIGS. 1A and 1B. The entire sequence of the mouse Oct-4 gene (Scholer et al. (1990) Nature 344:435–439) is contained on a 4.73 Kb BamHI fragment (FIGS. 2A, 2B, and 2C). There are five exons and four introns. The sizes of the two short introns, 2 and 4, are 182 and 139 bp, respectively; the sizes of introns 1 and 3 are approximately 2430 and 450 bp, respectively. The POU domain is encoded by two or three split exons. The cap site of the murine Oct-4 transcript is located 163 bp upstream of the start codon (Yeom, 1991).

The invention will now be described in more detail in the following non-limiting examples with reference to the drawings. The examples are for illustration only and do not limit the scope of the present invention in any way, which is defined only by the claims. All references cited are hereby incorporated by reference herein in their entirety.

EXAMPLE 1

Cloning of Porcine Oct-4

1.1 Obtaining Porcine Oct-4 Exon 4 Sequences

In order to obtain a fragment of porcine genomic DNA containing the Oct-4 sequence, degenerate PCR primers were designed based on sequence identity to several Oct family genes found in the Entrez database. These primers were designed such that they might amplify different Oct family members and were not specific for Oct-4. The sequences of the two degenerate primers are as follows:

DA34 (sense): 5' GCCCCTSCTGGAGAAGTGG 3' (SEQ ID NO:1)

DA37 (antisense): 5' GSCGSCGGTTRCAGAACCA 3' (SEQ ID NO:2)

DA34 maps within exon 3, which contains part of the POU-specific domain. DA37 maps within exon 4, which contains the POU-homeodomain.

Using a commercial source of porcine genomic DNA (Clontech, Palo Alto, Calif., catalog # 6651-2) as template, a PCR fragment of approximately 1 Kb was amplified using Touchdown PCR (Roux, 1994) with Vent DNA Polymerase (New England Biolabs, Inc. ("NEB") Beverly, Mass.) on a Perkin-Elmer 9600 Thermocyler (Perkin-Elmer Corp., Norwalk, Conn.). Following NEB's protocol for setting up PCR reactions, the samples were amplified as follows: The tubes were heated at 94° C. for 2 minutes followed by 3 cycles, each consisting of 45 seconds at 94° C., 1 minute at 55° C. and 2 minutes at 72° C. The 3-cycle PCR step was repeated for 14 cycles during which the annealing temperature was sequentially decreased by 1° C. every cycle. The final annealing temperature after 14 cycles was 40° C. Following this, 10 cycles were carried out at 94° C. for 45 seconds, 1 minute at 40° C. and 2 minutes at 72° C. A final extension for 5 minutes at 72° C. completed the PCR program.

The 1 Kb PCR fragment was purified by gel electrophoresis followed by clean up on Qiaex resin (Qiagen, Chatsworth, Calif.) according to its manufacturer's protocol. The PCR fragment was treated with Taq polymerase in order to add the 3' A overhang. This allowed the cloning of this fragment into the TA vector, pCR II (Invitrogen, San Diego, Calif.). Several clones were sequenced using the primer walking technique and standard DNA sequencing methodology. The complete sequence for clone pDA118-1 (960 bp) was determined. Based on sequence identity to both the human and mouse Oct-4, this clone was concluded to be authentic porcine Oct-4. The region of the Oct-4 gene contained within this clone extends from the last 48 bp of exon 3 to the first 27 bp of exon 5. Intron 3 was 628 bp, exon 4 was 159 bp and intron 4 was 99 bp in length.

1.2 Amplification, Cloning and Partial Sequencing of a Fragment from Porcine Genomic DNA which Extends from Exon 1 to Exon 4

A degenerate sense PCR primer within exon 1 was designed based on the sequence of human (Takeda et al. (1992) Nucleic Acids Research 20:4613–4620) and mouse Oct-4 (Okazawa et al. (1991) EMBO J. 10:2997–3005). The primer location was selected within the most conserved region of exon 1:

DA44 (sense): 5' CACCTGGCTTCRGAYTTCGCCTTC 3' (SEQ ID NO:3)

Using the DNA sequence derived from the 960 bp PCR fragment (clone PDA118-1), isolated from porcine genomic DNA (Clontech, Palo Alto, Calif.) and sequenced as described in 1.1 above, 2 antisense PCR primers were designed which map within either exon 3 or 4, respectively, and contain the following sequences:

DA43 (antisense, exon 3): 5' GCAGATTCTCGTTGTTGTCAGCTT 3' (SEQ ID NO:4)

DA58 (antisense, exon 4): 5' GTTGCCTCTCACTCGGTTCTCGATAC 3' (SEQ ID NO:5)

Using porcine genomic DNA (Clontech, Palo Alto, Calif.) as template, 2 PCR reactions were set up with either primer pair DA44/43 (SEQ ID NO:3/SEQ ID NO:4) or DA44/58 (SEQ ID NO:3/SEQ ID NO:5) using the TaKaRa LA Taq Kit (Pan Vera, Madison, Wis.). PCR conditions were as recommended by the manufacturer, namely: 94° C. for 2 minutes, 30 cycles at 98° C. for 15 seconds, then 65° C. for 11 minutes, followed by a 72° C. extension for minutes. The expected sizes of the PCR products ranged from 3.2 to 6.8 kb. The observed PCR products were ~4.2 Kb for exon ⅓ primers and ~5.1 Kb for exon ¼ primers.

The PCR products were purified by gel electrophoresis followed by clean-up on Qiaex resin (Qiagen, Chatsworth, Calif.). The purified fragments were cloned directly into the TA vector pCR II, transformed and bacteria colonies screened. Two clones were selected which contained either exon ⅓ fragment (pDA131-5) or exon ¼ fragment (pDA132-9). Large-scale DNA preparations were made of each of these clones using Qiagen DNA Kit. Using standard DNA sequencing methodology that included the use of the SequiTherm Cycle Sequencing Kit (Epicentre Technologies, Madison, Wis.) and their vector sequencing primers, both clones were sequenced in from both ends. Sequence comparison of pDA132-9 with the sequence from pDA118-1 derived in Example 1.1 confirmed that this clone was authentic Oct-4. Exon 3 sequence of the two clones was also very similar. A consensus exon 1 sequence was obtained from sequence data of both clones. Approximately 340 bp of exon 1 sequence was determined for porcine Oct-4, as shown in FIGS. 3A and 3B (SEQ ID NO:6). This sequence showed a high degree of sequence identity to both human and mouse Oct-4 sequences.

1.3 Obtaining an Oct-4 Exon 1 Probe

A second porcine Oct-4 probe was generated using the following oligonucleotide primers:

Oct-4 exon 1 5': 5' GGATCCTCGGACCTGGCTGAGCTTCCAA 3' (SEQ ID NO:7)

Oct-4 exon 3 3': 5' GAGCTCGTTGTTGTCAGCTTCCTCCACCCA 3' (inverse complement) (SEQ ID NO:8)

The oligonucleotide primer SEQ ID NO:7 includes nucleotides 92 through 118 of SEQ ID NO:6, while SEQ ID NO:8 was derived from the porcine exon 3 sequence.

Since the size in both the human and murine counterparts of porcine Oct-4, intron 1, is known to be quite large, i.e., 5 Kb and 2.43 Kb respectively (Takeda, 1992; Yeom, 1991), the PCRs were carried out using the TaKaRa LA Taq kit (Pan Vera Corp., Madison, Wis.). Each 50 $\mu l$ reaction contained 5 $\mu l$ 10× LA PCR buffer II, 5 $\mu l$ 25 mM $MgCl_2$, 8 $\mu l$ dNTP mix (2.5 mM each), 2.5 units of TaKaRa LA Taq (0.5 $\mu l$), 500 ng template DNA (porcine genomic DNA from Clontech (Palo Alto, Calif.) or from d/d miniswine #s 12021, 11378, 12023, 12037, 12038) and 100 pmol each oligonucleotide. The polymerase chain reaction (PCR) was performed using a Perkin Elmer DNA Thermal Cycler 480. The program used included 5 minutes at 94° C., followed by 14 cycles, each containing 20 seconds at 98° C. and 8 minutes at 68° C. This was followed by 16 cycles, each consisting of 20 seconds at 98° C. and 8 minutes at 68° C. with an autoextension time of 15 seconds/cycle. The program concluded with a final extension of 5 minutes at 72° C. and a 4° C. soak. All reactions, except one, produced two PCR products: a major band at approximately 4.5 Kb and a minor band at 0.6 Kb (miniswine # 12037 gave only the smaller band). These were the sizes one would expect from an intron containing gene and an intronless gene, respectively, within this portion of Oct-4.

The 4.5 Kb PCR fragment obtained from miniswine #12038 was gel isolated using Qiaex II resin (Qiagen Inc., Chatsworth, Calif.) cloned into the vector pCR II and the resultant plasmid transformed into *E. coli* Inv∞F' using the instructions provided with the TA cloning kit (Invitrogen, San Diego Calif.). In order to identify those clones which contained the Oct-4 insert, two oligonucleotides were ordered from Genosys Biotechnologies (The Woodlands, Tex.) and colony PCRs were performed. The two oligonucleotides are shown below:

Oct-4 Ex 1-5' seq: 5' CGGACCTGGCTGAGCTTCCAA 3' (SEQ ID NO:9)

Oct-4 Ex 1-3' seq: 5' CCTCGGAGTTGCTCTCCACC 3' (SEQ ID NO:10)

SEQ ID NO:9 contains nucleotides 98 through 118 of SEQ ID NO:6, and SEQ ID NO:10 contains the reverse complement of nucleotides 307 through 326 of SEQ ID NO:6.

Bacteria derived from each of 40 white (presumed to be insert containing) colonies were separately inoculated into 50 μl of distilled water. The 40 samples were boiled for 5 minutes and centrifuged briefly in order to pellet the cells. Ten μl of each supernatant then served as template for PCRs which were carried out as described previously for Taq DNA polymerase with the following exceptions: 1) the samples contained 50 μl rather than 100 μl and 2) the program used was 5' at 94° C., followed by 35 cycles, each containing 1 minute at 94° C., 1 minute at 55° C. and 1 minute at 72° C. There was a final extension of 10 minutes 72° C. followed by a 4° C. soak. The two oligonucleotides used in the PCRs should amplify a 230 bp exon 1 fragment of Oct-4. Most of the colonies tested were positive and one (#12) was chosen for sequence analysis. All sequencing was performed using either the Sequenase version 2.0 kit (United States Biochemical Corp., Cleveland, Ohio 44122) or the Fidelity DNA Sequencing kit (Oncor, Inc. Gaithersburg, Md. 20877). FIGS. 4A and 4B (SEQ ID NO:11) show the sequence of the 5' end of clone #12, which includes most of exon 1 and a small portion of intron 1. By sequence comparison to the human and murine sequences, the exon/intron junction is estimated to be at nucleotide 320. The amino acid sequence of exon 1, which shows strong homology to both the murine and human genes, is underlined.

In order to prepare an exon 1 probe for use in a genomic Southern as well as in a subsequent library screen, the oligonucleotide shown above as SEQ ID NO:10 and the following oligonucleotide (SEQ ID NO:12) were used in a PCR for which the 4.5 Kb Oct-4 insert of clone #12 served as template:

Oct-4 ex 1 probe 5': 5' GGATCCTCGGACCTGGCT-GAGC 3' (SEQ ID NO:12)

SEQ ID NO:12 includes nucleotides 92 through 112 of SEQ ID NO:6.

Ten identical PCRs, using Taq DNA polymerase, were carried out as described previously. A small portion of each reaction product was run on a 1% agarose gel in order to confirm the presence of a 236 bp band. The remainder of the reactions were then pooled, chloroform extracted, and ethanol precipitated. After resuspension in TE (10 mM Tris-HCl, pH 8.0, 1 mM EDTA), the DNA fragment was quantitated by running a portion on a 1% agarose gel along with markers containing known quantities of DNA.

1.4 Genomic Southern to Verify Utility of Oct-4 Exon 1 Probe

A genomic Southern was performed in order to determine whether or not the 236 bp probe, described in the previous section, would hybridize with specificity and thus could be safely used in a library screen (see *Molecular Cloning, a Laboratory Manual,* second edition, J. Sambrook et. al., Cold Spring Harbor Laboratory Press, 1989). The genomic DNA used in both the Southern blot and library construction was obtained from d/d miniswine # 11852. For the Southern, 20 μg/reaction of genomic DNA was digested at 37° C. overnight in a 50 μl volume with each of the following restriction enzymes: Bam HI, Bgl II, Eco RI, Hind III, Pst I, Sac I, Xba I (New England Biolabs, Inc., Beverly, Mass.). A small sample of each digest was run on a 0.7% agarose gel in order to insure that the digests were complete. The remainder of each of the 7 reactions was then ethanol precipitated, rinsed in 70% ethanol, dried, resuspended in 25 μl TE and run on a 15×15 cm 0.7% agarose gel overnight at 20 V. A positive control was also included on 2 lanes of the gel, i.e., 2 pg and 20 pg respectively of the 4.5 Kb Oct-4 insert obtained by PCR, as previously described.

The next morning, the gel was soaked in 0.25 N HCl for 10 minutes, rinsed in water, and the DNA denatured for 45 minutes by soaking the gel in 1.5 M NaCl, 0.5 M NaOH. After a water rinse, the gel was placed for 45 minutes in a neutralization solution containing 1.5 M NaCl, 1M Tris-HCl pH 7.4 and then for another 45 minutes in 10×SSC (1.5 M sodium chloride/0.15 M sodium citrate, pH 7.0). The DNA was transferred onto a nitrocellulose membrane in 10×SSC overnight using the TurboBlotter Rapid Downward Transfer System (Schleicher & Schuell, Inc., Keene, N.H. 03431). After transfer, the nitrocellulose membrane was rinsed for 5 minutes in 5×SSPE (0.75 M sodium chloride, 0.05 M sodium phosphate, 0.005M EDTA) and then baked for 2 hours at 80° C. in a vacuum oven.

Approximately 50 ng of the 236 bp probe was labeled by random priming with $\alpha$-$^{32}$P dCTP according to instructions provided with the High Prime DNA Labeling Kit (Boehringer Mannheim, Indianapolis, Ind.). The nitrocellulose blot was prehybridized at 65° C. for 3 hours in a solution containing 6×SSC, 5×Denhardt's (0.5 g Ficoll, 0.5 g polyvinylpyrrolidone, 0.5 g bovine serum albumin), 100 μg/ml sheared denatured herring sperm DNA, 0.75% sodium dodecyl sulfate (SDS). Hybridization was carried out overnight at 65° C. in the same solution to which the probe was added, following its denaturation in 1/10 volume 0.1 N NaOH. The blot was then washed 2×15 minutes at room temperature in 7×SSPE, 0.5% SDS, 2×15 minutes at 37° C. in 1×SSPE, 0.5% SDS, 1×15 minutes at 65° C. in 0.1×SSPE, 1% SDS, rinsed in 0.1×SSPE at room temperature and exposed to X-ray film for 2 days at −80° C.

The results indicated that the Oct-4 exon 1 probe was quite specific since only 1 or 2 bands appeared for each of the restriction digests performed. Hybridization of the probe to the positive control was also seen, but only in the lane which contained the higher concentration (20 pg) of DNA.

1.5 Construction of a Miniswine Haplotype d/d Genomic Library

Miniswine genomic DNA (11852, haplotype d/d) was extracted from liver tissue and partially digested with Sau3AI. The Sau3AI sites were then partially filled-in and the fragments were size fractionated by gel electrophoresis using standard methodology. The genomic fragments were ligated to LambdaGEM-12 XhoI partially filled-in according to manufacturer's instructions (Promega, Madison, Wis.), packaged using Stratagene's Gold extract and titered on *E. coli* KW251 host cells.

The genomic library had $1.5\times10^6$ independent clones, with an average insert size of ~12 Kb. The library was amplified one time, aliquoted and stored. The final titer of the amplified library was $1\times10^{10}$ pfu/ml. 1.6 Screening the miniswine haplotype d/d genomic library for Oct-4 exon 1-containing clones Approximately $3\times10^5$ clones were screened with the Oct-4 exon 1 probe using duplicate nitrocellulose filters (Sambrook, 1989). The prehybridization, hybridization and wash conditions were essentially the same as those used for the Southern blot. The first round screen produced 5 positives; each of these was replated at 3 different plaque densities and screened again with the Oct-4 exon 1 probe. Only 2 of the 5 were still positive after the second round screen. The two remaining clones (designated as #3 and #4 respectively) were plaque purified after a third round screen and λ DNA was prepared from plate lysates using a Qiagen Lambda Kit (Qiagen, Chatsworth, Calif.).

1.7 Mapping the Oct-4 Exon 1-containing Clones by PCR

Lambda clones #3 and #4 were mapped using LA PCR (Pan Vera, Madison, Wis.). The reactions were carried out as described previously except for a change in the program which increased all times at 68° C. from 8 to 12 minutes. Two new oligonucleotides were made based on sequence provided by Promega (Madison, Wis.), the supplier of the LambdaGEM-12 vector:

RK EMBL3L: 5' GCAACGAACAGGTCACTATCAGTCA 3' (left arm of vector) (SEQ ID NO:13)

RK EMBL3R: 5' CTGCCTTCATTAAGGGCTGCGCAC 3' (right arm of vector) (SEQ ID NO:14)

Figure 5A:
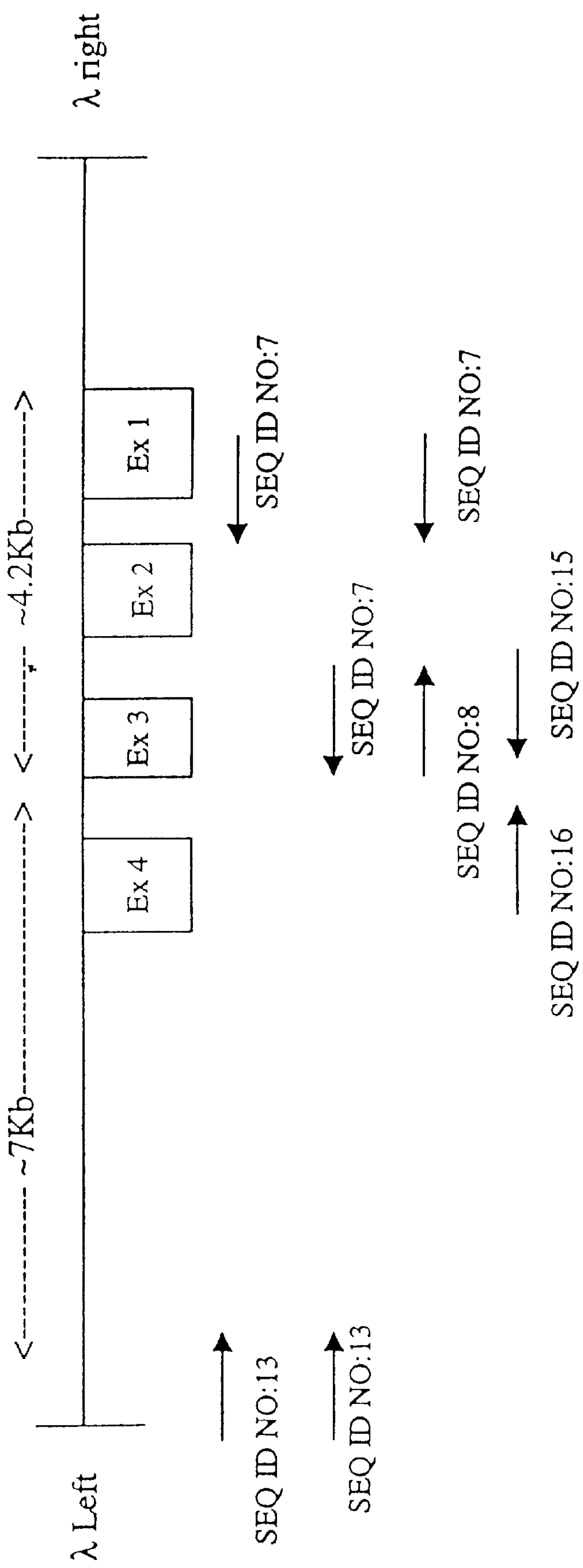
FIG. 5A illustrates the results obtained from PCR mapping of the did haplotype miniswine Oct-4 exon 1-containing Lambda clones #3.
Figure 5B:
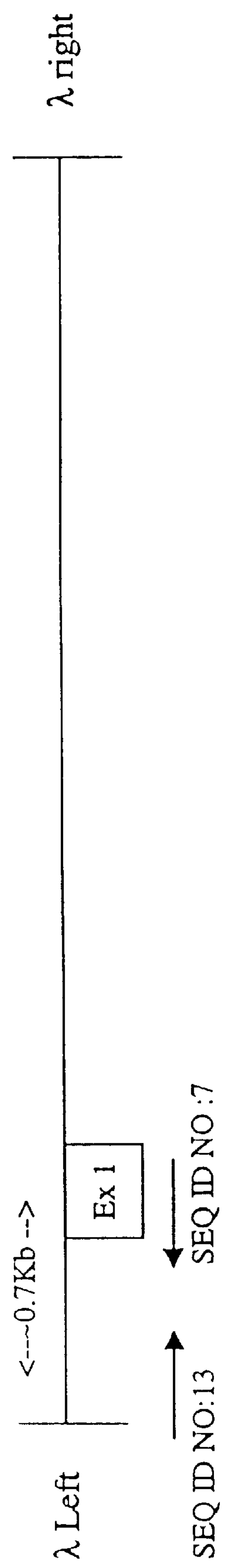
FIG. 5B illustrates the results obtained from PCR mapping of the d/d haplotype miniswine Oct-4exon 1-containing Lambda clone #4.

It should be pointed out that the oligonucleotide shown as SEQ ID NO:14 never gave a positive PCR result, nor did two other oligonucleotides designed to amplify portions of the Oct-4 clones from the right arm of the vector. As can be seen in FIG. 5, both clones are inserted in the vector with their 5' ends toward the right arm and their 3' ends toward the left arm of LambdaGEM-12. When the oligonucleotide pair of SEQ ID NO:7 and SEQ ID NO:13 was used, the size of the fragment amplified from clone #3 was approximately 11 Kb while the same pair amplified a much smaller 0.7 Kb fragment from clone #4. Additional PCRs using oligonucleotide pairs SEQ ID NO:15 and SEQ ID NO:13, SEQ ID NO:7 and SEQ ID NO:8, or SEQ ID NO:15 and SEQ ID NO:16 generated 7 Kb, 4.2 Kb, and 0.9 Kb products respectively from clone #3, but no products at all from clone #4. SEQ ID NO:15 includes sequences present in the porcine Oct-4 exon 4. SEQ ID NO:16 includes sequences in the exon 5/intron 4 junction region of porcine Oct-4. Oct-4 exon 3 5': 5' CTCGAGAAGTGGGTGGAGGAAGCGAC 3' (SEQ ID NO:15) Oct-4 exon 5/intron 4 3': 5'GAATTCCACGCGGACCACCTGAGAGCAGGA3' (reverse complement) (SEQ ID NO:16)

These PCR results indicated that clone #3 contained the entire coding region of Oct-4 (i.e. exon 1 through exon 5 in addition to all 4 introns), several kilobases downstream, plus 2–3 kilobases upstream; clone #4 appeared to consist mostly of exon 1 and upstream regions.

1.8 DNA Sequence Analysis of Lambda Clones #3 and #4

In order to obtain exon 1 containing fragments of Lambda clones 3 and 4 for DNA sequence analysis, a Southern blot was prepared and probed with the exon 1 probe described earlier. The following restriction enzymes were used to digest 1–2 μg of clones 3 and 4 respectively, in 25 μl reactions: Bam HI, Eco RI, Hind III, Sac I, Xba I. All digests were carried out for 6 hours at 37° C. and then loaded directly onto a 15×15 cm 1% agarose gel. The gel was run overnight at 20 V and the DNA transferred as described previously with the following changes: 1) instead of nitrocellulose, a positively charged nylon membrane was used, and 2) transfer was carried out in 20×SSC instead of 10×SSC.

The 236 bp exon 1 probe was labeled non-radioactively by random priming with DIG-11-dUTP. Labeling was carried out according to instructions provided with the Genius-2 DNA Labeling Kit (Boehringer Mannheim Corp., Indianapolis, Ind.). Following transfer, the DNA was affixed to the nylon blot by irradiation in a U.V. 1800 Stratalinker (Stratagene, La Jolla, Calif.). The blot was prehybridized for 3 hours at 50° C. in DIG Easy Hyb (Boehringer Mannheim) and then hybridized overnight at 50° C. in 15 ml of the same solution to which approximately 115 ng of boiled, denatured DIG-labeled probe had been added. Following hybridization, the blot was washed 2×15 minutes at room temperature in 2×SSC, 0.1% SDS, and then 2×15 minutes in 0.1×SSC, 0.1% SDS at 50° C. Oct-4 exon 1 containing bands were detected by chemiluminescence using the reagents Anti-Digoxigenin-alkaline phosphatase and the substrate CSPD, following instructions obtained from Boehringer Mannheim.

Four fragments which hybridized with the exon 1 probe, 2 from each Lambda clone (#3 and #4), were gel isolated using Qiaex resin and ligated into pBluescript KSII for sequencing. The resultant clones are described below:

1. 5D is a 5.5 Kb Bam HI fragment derived from Lambda clone #3. It contains exon 1, a portion of intron 1 and approximately 3 Kb upstream of exon 1.
2. 6A is a 4 Kb Sac I fragment derived from Lambda clone #3 which overlaps clone 5 D. It contains exon 1, slightly more than 1 Kb upstream, and contains 1 Kb more of intron 1 downstream than does 5D.
3. 9-5 is a 1.3 Kb Hind III fragment derived from Lambda clone #4.
4. 10-C is a 0.6 Kb Sac I fragment of Lambda clone #4 which overlaps the Hind III clone above.

Sequence analysis of the overlapping fragments derived from Lambda clone #4 indicated that they were not derived from authentic Oct-4. The exon 1 sequence was related, but not identical to sequence obtained previously. There was no open reading frame in this exon 1-like DNA stretch. Furthermore it was joined to a sequence which was similar (but not identical) to that of exon 2, but with no intron 1 between them. A portion of this sequence can be seen in FIGS. 6A and 6B. Since this clone did not appear to contain authentic Oct-4, no further sequence analysis was carried out on λ clone #4.

Figure 7:
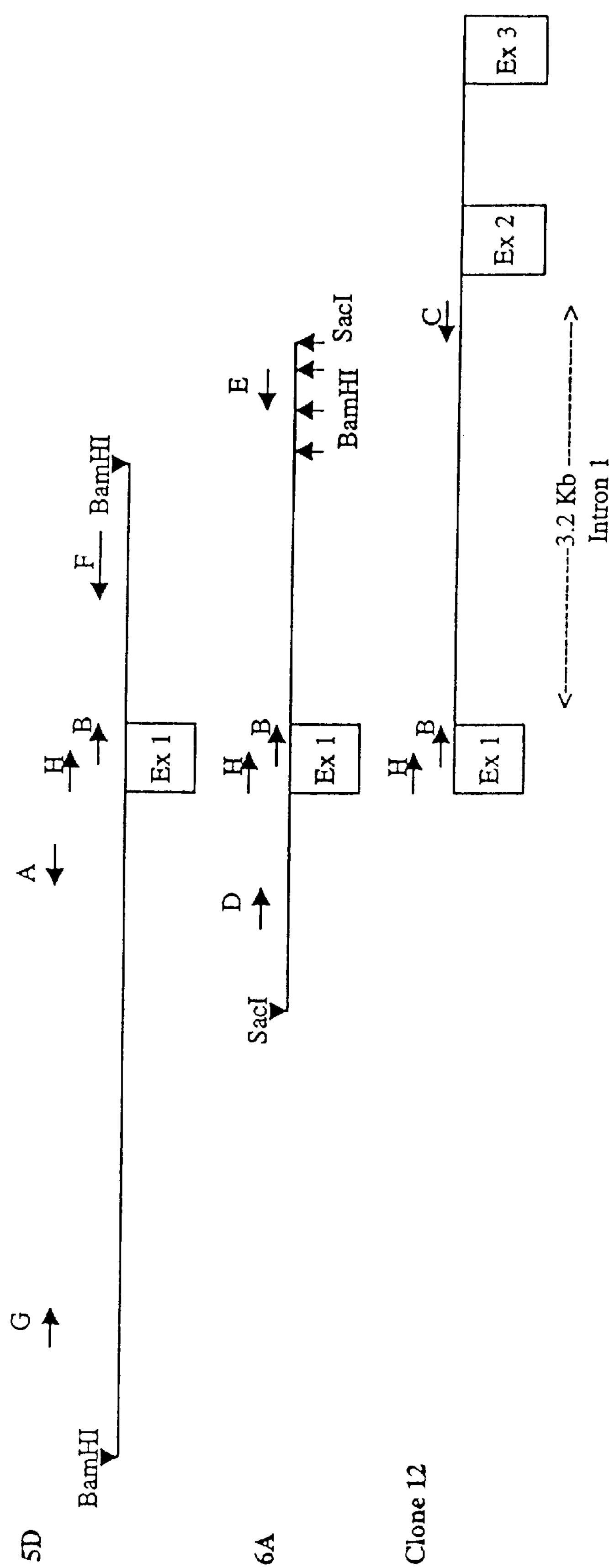
FIG. 7 shows the relationship between two fragments of porcine Oct-4, fragments 5 D and 6 A, derived from Lambda clone #3, and clone 12 (a PCR product encompassing a portion of exon 1 through exon 3). The letters A through H correspond to oligonucleotides used to map the fragments 5D and 6A derived from Lambda clone #3 and clone 12. Letter A corresponds to SEQ ID NO:7, letters B through H correspond to SEQ ID NO:17 through SEQ ID NO:23. The lengths of fragments derived for the various oligonucleotide pairs are as follows: G→F, 3.5 Kb; A→G, 2.2 Kb; F→H, 1.2 Kb; B→F, 0.9 Kb; D→E, 3 Kb; H→E, 2.3 Kb; and H→C, 3.5 Kb.

FIG. 7 shows the relationship between fragments 5D and 6A derived from Lambda clone #3 and clone 12, described earlier. Mapping was done by sequence analysis as well as by LA PCR, using a number of oligonucleotides (SEQ ID NO:7 and SEQ ID NO:17 through SEQ ID NO:23) which are identified by the letters A through H on FIG. 7. As can be seen, the 3 clones represent overlapping segments of porcine Oct-4 which extend from approximately 3 Kb upstream of exon 1 through exon 3. DNA sequence obtained from fragments 5D and 6A upstream of exon 1 further confirm that they are derived from authentic Oct-4. The murine counterpart of porcine Oct-4 (Oct3/4) lacks a TATA box (SEQ ID NO: 38), but possesses a putative Sp1/HRE (hormone-responsive element) in the proximal promoter region (Minucci et. al. (1996) EMBO J. 15:888–899). An identical sequence (see below) is found approximately 100 bp upstream of the translational start in the procine gene, which also lacks a TATA (SEQ ID NO: 38) box 5' GGGGGCGGGGCCAGAGGTCAAGGTCA 3' (SEQ ID NO: 39). The sequence determined for the promoter polynucleotide sequence of the porcine Oct-4 gene is shown in FIGS. 8A, 8B, and 8C (SEQ ID NO:24). This is what is referred to herein as Applicants' "Oct-4 promoter polynucleotide sequence" or the "Oct-4 promoter sequence". FIGS. 9A–C collectively show an alignment comparison of the human, mouse, and procine Oct-4 promoter oligonucleotide sequences. FIGS. 10A–C collectively show an alignment comparison of the Retinoic Acid Responsive Element (RARA) regions of the procine and murine Oct-4 promoter regions.

EXAMPLE 2

Testing of the Oct-4 Promoter

In order to demonstrate that the porcine Oct-4 promoter polynucleotide sequence is an embryonic stage specific promoter, the following constructs were made and tested in mouse embryonic stem cells.

2.1 Construction of pOct-4-βGeo

Plasmid pGT1.8 was obtained from Dr. P. S. Mountford (Stem Cell Sciences, Melbourne, Victoria, Australia). pGT1.8 contains a nuclear targeted Internal Ribosomal Entry Site (IRES)-βGeo construct. βGeo is a gene fusion of sequences encoding β-galactosidase and neomycin resistance gene (Friedrich et al. (1991) Genes & Development 5:1513–1523). 5' to the IRES is a sequence containing murine engrailed-2 splice acceptor which is designated as EN-2 (Gossler et al. (1989) Science 244:463–465). A 5.5 Kb fragment containing the porcine Oct-4 promoter, exon 1 and a portion of intron 1 was inserted into the SalI site of pGT1.8 as follows: Clone 5D (Example 1.8 above) was incubated with SalI/NotI and the 5.5 Kb DNA fragment was isolated. The DNA fragment was cleaved using Eco47III and the large 4.5 Kb 5'SalI/Eco47III DNA fragment was gel isolated.

A 0.6 Kb 3' portion of 5D was isolated after digestion with Eco47III/BamHI. The 3'BamHl site at the end of this fragment was converted to a XhoI site by PCR mutagenesis, using the following oligonucleotides:

PM Eco47III 5" 5' TCAAAGCGCTAAAATGTGATTTGG (SEQ ID NO:25)

PM XhoI3' 5' CGATCTCGAGGGATCCCAGACCGGG-GAACT (SEQ ID NO:26)

The resulting PCR product was cloned into the TA vector, pCRII (Invitrogen, San Diego, Calif.) and sequenced. A correct clone was identified, cleaved with Eco47III and XhoI and gel purified. The final construct was constructed by ligation of dephosphorylated pGT1.8/SalI, the 4.5 Kb SalI/Eco47III 5' portion of 5D, and the 0.6 Kb Eco47III/XhoI 3' fragment. Since SalI and XhoI generate compatible overhanging ends, the Oct-4 insert could be inserted into pGT1.8 in either of two orientations. These orientations can be distinguished by XbaI cleavage. There are two XbaI sites in pGT1.8 and three in the Oct-4 insert: 125, 950, and 1990 bp from the SalI site. The correct orientation results in the following size fragments upon XbaI digestion: 5.3 Kb, 4.9 Kb, 3.0 Kb, 1.0 Kb, and 0.8 Kb. XbaI cleavage of the incorrect orientation generates 6.3 Kb, 4.9 Kb, 2.0 Kb, 1.0 Kb, and 0.8 Kb fragments.

2.2 Construction of pPGK-βGeo

The mouse PGK promoter was removed from a PGKneo vector (Aron Thall, BioTransplant, Inc.) using EcoRI and PstI. The resulting 0.5 Kb fragment was gel purified and the overhanging ends were filled in with Klenow DNA polymerase (NEB, Beverly, Mass.) according to instructions, phenol-chloroform extracted, and ethanol-precipitated. The DNA was resuspended in 1.5 μl $H_2O$, and 2 μg of phosphorylated HindIII linkers (2 μl) was added together with 1 μl 10 mM ATP, 1 μl 100 mM DTT, 2 μl 10× ligation buffer (Novagen, Madison, Wis.), and 1.5 μl T4 DNA ligase. The ligation reaction was incubated overnight at 16° C. The resulting DNA was digested with EcoR1 and HindIII and gel-purified. pOCUS-2 (Novagen, Madison, Wis.) was digested with EcoRI and HindIII and desphosphorylated using shrimp alkaline phosphatase (SAP). A ligation was performed with the pOCUS-2 fragment and the mouse PGK-promoter fragment. Following transformation of *E. coli,* colony PCRs were performed using primers that correspond to sequences located on either side of the multiple cloning site (MCS). The PCR template was DNA released from bacterial colonies which had been boiled for 5 minutes. A correct clone was grown up, plasmid DNA was prepared using a Qiagen column (Qiagen, Chatsworth, Calif.) and the DNA digested with HindIII and phosphatased.

A polynucleotide fragment containing the βGeo coding sequence was isolated from a vector provided by P. S. Mountford (Stem Cell Sciences, Melbourne, Australia). The plasmid was digested with ScaI and HindIII and the 4.3 Kb HindIII fragment containing βGeo and the polyadenylation site was gel isolated. A HindIII digest alone would have resulted in two fragments of approximately equal size, therefore ScaI was added in order to digest the unwanted DNA fragment into two smaller fragments.

A ligation was performed using the pOCUS-2/PGK promoter, linearized by HindIII and phosphatased, and the HindIII βGeo fragment. Following bacterial transformations, colony PCRs were carried out in order to identify a correct clone which contained the HindIII fragment in the correct orientation. The 5' PCR primer (5'AGCGCACGTCTGCCGCGCTGTT (SEQ ID NO:27)) is located in the PGK promoter, while the 3' primer (5'CCTGTAGCCAGCTTTCATCAAC (SEQ ID NO:28)) is in the βGeo fragment.

2.3 Construction of pPGK-EGFP

The EGFP derived plasmids were based upon the plasmid pEGFP-1 (Clontech, Palo Alto, Calif.; Genbank Accession #U55761) which encodes a variant of the green fluorescent protein used for monitoring the activity of promoters cloned into the multiple cloning site. EGFP is human codon-optimized and contains a chromophore mutation which produces fluorescence 35 times more intense than wild-type GFP. Sequences flanking the EGFP gene have been converted to a translation initiation consensus ribosome-binding site to further increase the translation efficiency in eukaryotic cells. The vector backbone provides an SV40 origin of replication and polyadenylation sequence, and a neomycin-resistance cassette for selection of stably transformed mammalian cells. One construct that served as the negative control was pEGFP without further modification.

pPGK-EGP was designed to contain the mouse PGK promoter driving expression of EGFP and was used as a positive control. The vector was constructed as follows: The vector pEGFP was digested with EcoRI and PstI and phosphatased. The PGK promoter was isolated by digestion of pPGKneo (Aron Thall, BioTransplant, Inc.) using EcoRI and PstI. The two fragments, linearized pEGFP and the PGK promoter, were ligated. After transformation of *E. coli,* miniprep DNA was prepared (Qiagen, Chatsworth, Calif.) and correct clones were identified following digestion with EcoRI and PstI.

2.4 Construction of pOct-4-EGFP

The experimental construct, pOct-4-EGFP, contained the 3.2 Kb portion of the porcine Oct-4 promoter. The construct was made as follows: 5D was digested with BamHI, and the 5.5 Kb insert containing the porcine Oct-4 promoter sequence plus exon 1 and part of intron 1 was gel purified, and digested again with BstBI and FspI. The 2.84 Kb BamHI/BstBI fragment was gel purified. (The FspI was added to the digestion reaction in order to cleave an unwanted 3 kb fragment). The remaining 0.36 Kb portion of the promoter was obtained by PCR, using the 5D insert as template, and the following primers:

Oct-4-BstBI 5' 5' CAGGGTCTTCGAAGAGGGGTCCA (SEQ ID NO:29)

Oct-4-SalI 3'5'GTCGACCAGGGCTCTCCAAGGGGA (SEQ ID NO:30)

This resulted in the addition of a SalI restriction site to the 3' end (SalI) which could be used for cloning purposes in pEGFP-1. Following PCR, the 0.36 Kb product was cloned into the TA vector (pCRII) and sequenced. After a correct clone was identified, a ligation was performed with the following DNA fragments: (1) pEGFP-1 digested with BamHI and SalI, and phosphatased; (2) the 2.84 Kb BamHI/BstBI portion of the Oct-4 promoter sequence; and (3) the 0.36 Kb BstBI/SalI 3' end of the Oct-4 promoter. Following transformation of *E. coli,* correct clones were identified by colony PCRs using the following primers:

5'GTCGACCAGGGCTCTCCAAGGGGA (SEQ ID NO:30)

6-T7 OL.4 5' 5'ACTTAGCACAGACACCASGACCT (SEQ ID NO:31)

A correct clone yields a 0.4 kb PCR product.

2.5 Cell Culture

Mouse RW4 embryonic stem cells (ES) and mouse embryonic fibroblasts (MEFs) were obtained from Genome Systems (St. Louis, Mo.). The ES cells had been isolated from the inner cell mass of a 3.5 day embryo from the mouse strain 129/SvJ; the MEFs had been isolated from 14.5 day embryos. The ES cells were cultured in 80% DMEM, 15% FCS (#A-1115-L, Hyclone, Logan, Utah), 2 mM L-glutamine, 0.1 mM non-essential amino acids, 10 mM HEPES, Pen/strep (100 units/ml), and 72 μM 2-mercaptoethanol. The ES cells were maintained in the presence of murine leukemia inhibitory factor (LIF, final concentration 1000 U/ml, Gibco/BRL, Gaithersburg, Md.). The MEFs were grown in 87% DMEM, 10% FCS, 2 mM L-glutamine, and 0.1 mM non-essential amino acids.

2.6 Transfections and Selection

Transfections were performed by electroporation as follows: The cells were washed twice with phosphate-buffered saline (PBS), trypsinized using Trypsin/EDTA (0.05%/0.53 mM), and centrifuged. Colonies of $0.4–1.0\times10^7$ cells were transfected with 25 μg linearized DNA (sequences from sections 2.1, 2.2, 2.3 and 2.4 as described above) in 800 μl electroporation buffer (20 mM HEPES, pH 7.05, 137 mM NaCl, 5 mM KCl, 6 mM D-glucose, 0.7 mM $Na_2HPO_4$) in a 0.4 cm cuvette using 300 v and 500 μF, at room temperature. The cells were seeded in 100 mm dishes ($2.5\times10^6$ cells/dish), containing a confluent monolayer of 30 Gy irradiated MEF. 24 hours later, the media was exchanged with selection medium containing 470 μg/ml G418. On day 8, G418 resistant colonies were picked and transferred to a 96-well plate that contained 50 μl trypsin solution. After 10 minutes, the cells were transferred to a 48 cell plate that contained medium plus 240 μg/ml G418. After three days, the medium was changed to 470 μg/ml G418 containing medium.

2.7 X-Gal (5-Bromo-4-Chloro-3-Indolyl β-D-Galactopyranoside) Staining Assay

The medium was removed from the culture dishes and the cells were washed briefly with PBS. Fixation solution (0.2% glutaraldehye, 0.1 M phosphate buffer, pH 7.3 [4 volumes 0.1 M disodium orthophosphate+21 volumes 0.1 M sodium dihydrogen orthophosphate], 2 mM $MgCl_2$, 5 mM EGTA) was added to the cells for 5 minutes at 4° C. The cells were washed three times for 10 minutes each time with wash solution (0.1 M phosphate buffer, pH 7.3, 2 mM $MgCl_2$). The staining solution was added (1 mg/ml X-Gal [Sigma, St Louis Mo.] final concentration prepared by dissolving 25 mg X-Gal in 500 μl N,N dimethyl formamide, mixed with 25 ml of washing solution with 41 mg potassium ferricyanide and 52.5 mg potassium ferrocyanide) overnight at 37° C. The stained plates were stored in 0.2% glutaraldehyde at 4° C.

2.8 Retinoic Acid Assay

A stock solution of all trans-retinoic acid (Sigma, St. Louis, Mo.) was prepared by dissolving it in absolute ethanol to a final concentration of 1 mM.

The cells were seeded in 24-well plates containing a feeder layer of irradiated MEFs. After 3 days, the media was adjusted to 0.5 μM retinoic acid. The medium was changed every 2–3 days. After 5 days, the medium was removed and fresh medium without retinoic acid was added to the cells. Cells were split if necessary to avoid confluency. The colonies were then stained using the X-gal procedure.

2.9 X-Gal Staining of Cells Transfected with the Various Vectors

The results (Table 1) demonstrate that the number of colonies derived from transfections using the PGK and Oct-4 promoter-containing plasmids was 50–100 fold higher than the number of colonies derived from the transfection using the promoterless plasmid. Therefore, the DNA sequence shown in FIG. 8, isolated from porcine genomic DNA, contains the porcine Oct-4 promoter sequence. The single clone that resulted from the transfection using the promoterless plasmid was demonstrated to express the βGeo fusion protein. This clone proved to be useful as a control for subsequent experiments as a non-developmentally regulated promoter. As used herein the staining legends indicate the following: XXX indicates a strong stain, XX indicates a moderate stain, and X indicates a weak stain.

TABLE 1

Transfection Efficiency and X-Gal Staining of Neomycin Resistant

| VECTOR | TOTAL # COLONIES | X-GAL STAINING |
|---|---|---|
| pβGeo - no promoter control | 1 (1 colony/5 × $10^6$ cells) | XXX |
| pPGKβGeo (pOCUS-2) | 9 (24 colonies/$10^6$ cells) | XXX |
| pOct-4-βGeo (pGT1.8) | 90 (12 colonies/$10^6$ cells) | XX |

Legend:
X-weak stain
XX-moderate stain
XXX-strong stain 2.10 X-Gal Staining after Treatment of Cell Cultures with Retinoic Acid The results of the X-Gal staining assay using cells that had been treated with retinoic acid are shown in Table 2. Cells grown derived from the single colony that was obtained from the pβGeo plasmid transfection differentiated in the absence of LIF. These differentiated colonies expressed the β-Geo fusion protein, further establishing that the promoter driving the expression of this protein was not regulated by the presence of retinoic acid in the culture medium.

Cells from the colonies that were derived from the pPGKβGeo transfection also underwent differentiation in the presence of retinoic acid in the culture medium, with only undifferentiated cells from one colony (A5) surviving as a mixed population of differentiated and undifferentiated cells. This result was expected due to the understanding that the PGK promoter is differentially regulated by the presence of retinoic acid (Sutherland et al. (1995) Gene Expression 4:265–279). The differentiated cells did not stain with X-Gal, indicating that indeed the PGK promoter was not active in these differentiated cells. These cells functioned in this assay as the positive control. The cells from the pOct-4βGeo derived colonies also differentiated in the presence of retinoic acid, with the resulting cell population being a mixture of a few undifferentiated cells together with a lot of differentiated cells. The undifferentiated cells stained with X-Gal but the differentiated cells did not. These results indicate that the porcine Oct-4 promoter is differentially regulated by the presence of retinoic acid in the culture medium. (Since retinoic acid promotes differentiation of the cells, it results in the turning off of the porcine Oct-4 promoter sequence because the sequence is only active in embryonic stem cells and not in differentiated cells.)

TABLE 2

X-Gal Staining of Colonies after Treatment of Cell Cultures with Retinoic

| Vector | LIF | G418 | Name of Colony | Undifferentiated colonies/well | Differentiated colonies/well | X-gal staining of undifferentiated colonies | X-gal staining of differentiate colonies |
|---|---|---|---|---|---|---|---|
| pβGeo | – | – | A2 | NO | XXX | na | XX |
| pPGKβGeo | – | – | A2 | NO | XXX | na | NO |
| | | | A3 | XX | XXX | X | NO |
| | | | A5 | X | XXX | X | X |
| pOct4βGeo | – | – | F4/A | X | XXX | X | NO |
| | | | E3/A | NO | XXX | na | NO |
| | | | E5/A | XX | XXX | X | NO |
| | | | E8/A | X | XXX | X | NO |
| | | | B1/A | X | XXX | X | NO |
| | | | E6/B | X | XXX | X | NO |
| | | | A1/B | XX | XXX | X | NO |
| | | | D2/B | XX | XXX | X | NO |
| | | | C3/B | NO | XXX | na | NO |

Legend:
X - weak stain
XX - moderate stain
XXX - strong stain

An alternate method for inducing differentiation of ES cells is to culture them in the absence of LIF. Colonies were grown in the absence of a feeder layer but in the presence of G418 selection, for 12 days, and then subjected to the X-Gal staining protocol. The results are presented in Table 3. The effects of the absence of LIF upon the ability of the pβGeo derived cells to undergo differentiation was less pronounced than the retinoic acid induced differentiation, but cells that did differentiate retained the ability to express the βGeo fusion protein, as expected.

Cells derived from the pPGKβGeo transfection did undergo differentiation, but did not lose the ability to express genes from the PGK promoter and therefore survived in the presence of G418. These results confirmed differences in the mechanism and/or extent of differentiation of ES cells induced by the absence of LIF but in the presence of retinoic acid or G418. The differentiated cells retained the ability to be stained by the X-Gal protocol.

Cells derived from the pOct-4βGeo transfections were similarly able to differentiate in the absence of LIF but did not express the βGeo protein. The cells appear to be differentially sensitive to the presence of G418, since some cells were still capable of proliferation despite the down-regulation of the pig Oct-4 promoter.

TABLE 3

X-Gal Staining of Cells Grown in the Absence of LIF, but in the Presence of G418 Selection

| Vector | LIF | G418 | Name of Colony | Undifferentiated colonies/well | Differentiated colonies/well | X-gal staining of undifferentiated colonies | X-gal staining of differentiate colonies |
|---|---|---|---|---|---|---|---|
| pβGeo | – | + | A2 | XXX | X | XXX | X |
| pPGKβGeo | – | + | A2 | X | XXX | X | X |
| | – | + | A3 | X | XX | XX | X |
| | | | A5 | XX | XX | X | X |
| pOct4βGeo | – | + | F4/A | X | XX | X | NO |
| | – | + | E3/A | X | XX | X | NO |
| | – | + | E5/A | X | XX | X | NO |
| | – | + | E8/A | X | XX | X | NO |
| | – | + | B1/A | XXX | XX | XXX | NO |
| | – | + | E6/A | XX | XX | XX | NO |
| | – | + | A1/B | XX | XX | X | NO |
| | – | + | D2/B | XX | XX | XX | NO |
| | – | + | C3/B | X | X | X | NO |

Legend
X - weak stain
XX - moderate stain
XXX - strong stain

Transfection of Porcine Oct-4/EGFP in Mouse ES Cells

Linearized plasmid DNAs were co-transfected with pPGKneo in a 1(PGK-Neo):10 (pOct-4/EGFP) ratio. Cells were selected for the ability to grow in 470 μg/ml G418. On day 7 fluorescent positive colonies were picked. No colonies grew from the promoterless control transfection; six colonies grew from the pPGK-EGFP transfection, representing six colonies/million cells plated; eleven colonies grew from the pOct-4-EGFP transfection, representing 3 colonies/million cells plated. Colonies were subjected to the retinoic acid differentiation protocol, namely the colonies were grown in 0.5 μM retinoic acid for 5 days, then 7 days without retinoic acid (growing on MEFs). After this treatment all of the colonies lost the ability to fluorescesce, thus confirming that the pig Oct-4 promoter is developmentally regulated and hence is an ES cell-specific promoter.

As described above, Applicants' have provided the porcine Oct-4 promoter polynucleotide sequence which enables one to selectively propagate large numbers of porcine embryonic stem cells. Once this is accomplished, one skilled in the art is then able to create a transgenic pig line which will comprise the cells which will express the selectable marker under the control of the porcine Oct-4 promoter sequence. Technology to create such a transgenic animal is known in the art and can be found, for example, in Transgenic Animal Technology, A Laboratory Handbook ((1994) ed., Carl A. Pinkert, Academic Press, Inc., San Diego, Calif.).

Additionally, one skilled in the art may propagate large numbers of stem cells by utilizing the selectable marker under the control of the porcine Oct-4 promoter polynucleotide sequence as described above, and then further genetically modify these cells to accomplish a desired activity or to eliminate an activity (e.g., to eliminate α1,3 galactosyltransferase activity). (See, e.g., Tearle et al. (1996) Transplantation 61:13–19 entitled "The α1,3 galactosyltransferase Knockout Mouse: Implications For Xenotransplantation."). These cells that have been further genetically modified are then capable of being used to generate a transgenic pig line containing cells, and organs, with the desired genetic activity or eliminated activity.

Although the invention has been described with reference to its preferred embodiments, other embodiments, can achieve the same results. Variations and modifications to the present invention will be obvious to those skilled in the art and it is intended to cover in the appended claims all such modification and equivalents and follow in the true spirit and scope of this invention.

We claim:

1. An isolated polynucleotide comprising the sequence of SEQ ID NO: 24.

2. An isolated polynucleotide comprising a sequence at least 95% identical to the sequence of SEQ ID NO: 24.

3. An isolated polynucleotide comprising a sequence at least 98% identical to the sequence of SEQ ID NO: 24.

* * * * *

UNITED STATES PATENT AND TRADEMARK OFFICE

CERTIFICATE OF CORRECTION

PATENT NO. : 6,482,937 B1
DATED : November 19, 2002
INVENTOR(S) : Mandred W. Baetscher It is certified that error appears in the above-identified patent and that said Letters Patent is hereby corrected as shown below:

Column 3,
Line 35, delete "did haplotype" and insert therefor -- d/d haplotype --

Column 7,
Line 46, delete "polynucleode" and insert therefor -- polynucleotide --

Signed and Sealed this

Thirtieth Day of September, 2003

JAMES E. ROGAN
*Director of the United States Patent and Trademark Office*

SEQUENCE LISTING

```
<160> NUMBER OF SEQ ID NOS: 39

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence:Degenerate
      primer for PCR amplification of Oct-family member
      gene

<400> SEQUENCE: 1

gcccctsctg gagaagtgg                                                19


<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence:Degenerate
      antisense primer for PCR amplification of
      Oct-family member gene

<400> SEQUENCE: 2

gscgscggtt rcagaacca                                                19


<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:Degenerate
      sense primer for PCR amplification of porcine
      genomic DNA corresponding to exon 1 of mouse and
      human OCT-4 genes

<400> SEQUENCE: 3

cacctggctt crgayttcgc cttc                                          24
```

-continued

```
<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:Antisense
      PCR primer mapping within exon 3 of porcine OCT-4

<400> SEQUENCE: 4

gcagattctc gttgttgtca gctt                                          24


<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence:Antisense
      PCR primer construct mapping within exon 4 of porcine OCT-4

<400> SEQUENCE: 5

gttgcctctc actcggttct cgatac                                        26


<210> SEQ ID NO 6
<211> LENGTH: 340
<212> TYPE: DNA
<213> ORGANISM: Artificial Sequence
<220> FEATURE:
<223> OTHER INFORMATION: Description of Artificial Sequence:Consensus
      sequence of exon 1 clones of porcine OCT-4 gene

<400> SEQUENCE: 6

gaattcggct tcaccaggct tcggacttcg ccttctcgcc cccgccgggc ggtggaggcg     60

atgggccggg agggcggagc cgggctgggt tgatcctcgg acctggctga gcttccaagg    120

gcctcccggt gggtcaggga tcgggccggg ggttgggccg ggcgccgagg tgtgggggct    180

tcccgcgtgc cccccgccct atgacttctg cggagggatg gcctactgcg cacctcaggt    240

cggagtgggg ctggtgcccc agggcggcct ggagacccct cagcccgagg gcgaggcggg    300

ggccggggtg gagagcaact ccgagggggc ctccccccgag                         340


<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide primer that includes nucleotides 92 - 118 of
      SEQ ID NO:6

<400> SEQUENCE: 7

ggatcctcgg acctggctga gcttccaa                                      28


<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide primer derived from the sequence of exon 3 of
      porcine OCT-4

<400> SEQUENCE: 8

gagctcgttg ttgtcagctt cctccaccca                                    30


<210> SEQ ID NO 9
<211> LENGTH: 21
```

-continued

```
<212> TYPE: DNA
<213> ORGANISM: Artificial Sequence
<220> FEATURE:
<223> OTHER INFORMATION: Description of Artificial Sequence:
      Oligonucleotide probe containing nucleotides 98-118 of SEQ ID NO:6
      used to identify OCT-4 inserts

<400> SEQUENCE: 9

cggacctggc tgagcttcca a                                             21


<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide probe containing reverse complement of nucleotides
      307-326 of SEQ ID NO:6

<400> SEQUENCE: 10

cctcggagtt gctctccacc                                               20


<210> SEQ ID NO 11
<211> LENGTH: 407
<212> TYPE: DNA
<213> ORGANISM: Sus scrofa

<400> SEQUENCE: 11

ggatcctcgg acctggctga gcttccaagg gcctcccggt gggtcaggga tcgggccggg     60

ggttgggccg ggcgccgagg tgtgggggct tcccgcgtgc cccccgccct atgacttctg    120

cggagggatg gcctactgcg cacctcaggt cggagtgggg ctggtgcccc agggcggcct    180

ggagacccct cagcccgagg gcgaggcggg ggcccgggtg gagagcaact ccgagggggc    240

ctcccccgag ccctgtgccg cccccgctgg cgccgcgaag ctggacaagg agaagctgga    300

gccgaacccc gaagaggcga gtgagctgcc gggagctggg ggaggcgatc gcgctggccg    360

ggggcgcacg caggggaggt ggtcgcctgc cgcccgggca ggaggg                   407


<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide probe for exon 1 of porcine Oct-4 inserts

<400> SEQUENCE: 12

ggatcctcgg acctggctga gc                                            22


<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide primer for left arm of Lambda vector containing
      exon 1 of porcine Oct-4

<400> SEQUENCE: 13

gcaacgaaca ggtcactatc agtca                                         25


<210> SEQ ID NO 14
<211> LENGTH: 24
<212> TYPE: DNA
<213> ORGANISM: Artificial Sequence
```

```
<220> FEATURE:
<223> OTHER INFORMATION: Description of Artificial Sequence:
      Oligonucleotide primer  for right  arm of Lambda vector containing
      exon 1 of porcine Oct-4

<400> SEQUENCE: 14

ctgccttcat taagggctgc gcac                                          24


<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide probe containing part of exon 4 of porcine Oct-4

<400> SEQUENCE: 15

ctcgagaagt gggtggagga agctgac                                       27


<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence:Synthetic
      oligonucleotide for PCR and containing reverse
      complement to part of exon 5/intron 4 of porcine
      Oct-4 gene

<400> SEQUENCE: 16

gaattccacg cggaccacct gagagcagga                                    30


<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence:Probe for
      mapping and sequence analysis of porcine OCT-4
      containing clones.

<400> SEQUENCE: 17

aaactgaggc ggagggtgtt tgct                                          24


<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence:Probe for
      mapping and sequence analysis of porcine OCT-4
      containing clones.

<400> SEQUENCE: 18

gcgagtgagc tgccgggagc t                                             21


<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence:Probe for
      mapping and sequence analysis of porcine OCT-4
      containing clones.

<400> SEQUENCE: 19

gcagaagacc attcagtgga aag                                           23
```

-continued

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence:Probe for mapping and sequence analysis of porcine OCT-4 containing clones.

<400> SEQUENCE: 20
cccgaaaact gtacggaatg gaa 23

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence:Probe for mapping and sequence analysis of porcine OCT-4 containing clones.

<400> SEQUENCE: 21
gaggaaaggg acaggaggaa ctg 23

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence:Probe for mapping and sequence analysis of porcine OCT-4 containing clones.

<400> SEQUENCE: 22
gtgaggtcta agggcttagt att 23

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence:Probe for mapping and sequence analysis of porcine OCT-4 containing clones.

<400> SEQUENCE: 23
cacagggtgc tatttagtcg g 21

<210> SEQ ID NO 24
<211> LENGTH: 3215
<212> TYPE: DNA
<213> ORGANISM: Sus scrofa

<400> SEQUENCE: 24
ggatccctag cctggaaacc tccataagcc gtgggtactg ccctaagaag aaaaaaaaag 60
tggtttgcta ccctggtcta gagcaagcct ccattttccc caggagtcat ttcagctggt 120
tttccctacc aaacagcaag gggatggccg ggctgacagc agcaaagtca ctgtcacctc 180
tttgcagcct tgccaggcca gctgcatctg gcagggagcg gcagctctca cctgccctcc 240
ctgggtcatg ctctacagcc agatacttgg catttgtctt tgtgtagggc ctcaatattg 300
tactctaata agggtacatg tgggagttcc ctggtggctc agcagttgag gatctggcat 360
tgtcactgct ctggcatgga tctctgctct ggcgcaggtt caattcctgg cctgggaact 420
tctgtacgcc gcaggcgtga ctggaaaaat acaggtgggg tggggtgagg agtgtatgtg 480

-continued

```
gagagtctgc aaacccaggc ctaaattggt ttgggggact tgaagttttt agtgactccc    540
tacccaaaag agtggagaag ccaggtctga tgacttaacc ccacttgcag tctgctctgg    600
gcctgcagag acctggcctc tgcagaagtg aagctgccta cacttcaggc ctaacaggag    660
ggtggggagg agaggggaat aggctcagcc ctgccatgcc aagcaccccc aggctgacta    720
ggactccaga caaatttagc ttgtccttaa ggttctgggt cagaccccag gcaagcacag    780
aactgatctg gctcagatgt ctggctacaa gctatccagg aacccaggca tccagccctc    840
cccagccctc cccaggcttt ccctctggaa taggaaggac acttgcttaa accagaaaca    900
taccatctag agcagctatt tatggtgatc taaaaaacac agggtgctat ttagtcgggg    960
gtgggtggga agggagaagg tgtttagggt ccgcgggaaa gtcaggggca caggggctct   1020
ctggaccaca tggggagagg ggtttctggg aggccagagg gcgaggagcc aaggagctca   1080
gcagtagatt ccctaggccc gcccctcccc ctcctcaggg aggccgtctt cttggcagac   1140
agcagataga tgcatgacaa aggggccatg atggctctgt cctggggggtt ggggagatgg  1200
ctagggaggg gcccctcctg gtctgaagca catctttcca cccccaccag gccccttaat   1260
ctatctgctt ttggggcagt tagtagttta gagttgaaat agctccagcc ctgctgccct   1320
ataaatcttt caacagacct atgggaagta ttgaaatgca tgcacgcaat tagtcacccc   1380
aaacgcacag gccgatgggc actggaagag attcagagga gaaaaagcaa aacaaaacaa   1440
cacggacaca caaaaaccca acagactcaa aggactcctg gtggagctaa ctggtcacag   1500
tctggaggat gccagcccct caagacagat gccgagccac tgaccctagc aaacaacctc   1560
agacccagcc aagatgaaga ggtgtctagg tccgcagagg tctgtgtccc agtctcagga   1620
gtctggcctc caaactgtag gaagctctga tccatggctt ctctggagag ccccccctcac   1680
tcaggttcac ctggggcctt cgtttagggc aagttggggg agcagacaga caaacatcat   1740
ccccagcaga cagccagtct gaaagctatt ctcttgcaaa cagaatcaag cactaggcca   1800
gcagcctgag cctcaggaca gacccagaaa aatagaccct gtgggagagc ttagggcagg   1860
attcctgcac cccctcccca atcgcagttc accccccttct gcatcttttc gctagccccc  1920
caaacaaagg cctggacgcc tcagtcctct agaggggggga caggatacct aggtcccagt  1980
gggggggccct gtctgaggct cagtctttga ggggatgggg gtgttgttgc tggagctctt  2040
ttagctgctc tgaaggggat tctgtgtgag ggggattgggg ctggggggtt gggggggcagg 2100
aagctgtccc caggggagcc atccaggccc attcaagggt tgagcacttg tttagggtta   2160
gagctgcccc ctctggggac caggattgtc cagccaaggc cattgtccgg ccccccttccc  2220
ccagtccctc ccaagcctct ttgaacctga agtcagatat ttttctctcc cccccccctcc  2280
ctccttggct ttccccaccc agggcctagg ggtggaggcc cagattggga ggtgggggag   2340
ggagaacagt caactatggg gctagatatt tgggtccctg aagggggggct gggggacaag  2400
gaacctgatg tgcgcgggga cccacagcgg gggacctgcg agcgggtgtc cgattgattc   2460
ctctgcctgc acaaagattg ggagactcag gcccagtcca tcgagcttga tccctggaag   2520
ggaaaatggg ggttccatcc ctgggtctgg tggaagggag gccccggaac ccggaaaact   2580
gtacggaatg gaagcccgtg tggcagtctg cccctggtga ggggtggaat ctaataggct   2640
gggcggatgg ttgctgggca tcgcagcttt ggggtgccgg aatctggcca gtaatctagt   2700
tgggaatgcc taggttcccg gactgggggt gagggcagag agcaggaatt gaggagtagc   2760
tccggcagga cttagcacag acaccagacc tgtgtgagga cctgagaggg tcgctggggt   2820
```

-continued

```
ccccttgagga gacagtgcca gggtcttcga agaggggtcc aacacctggc tccccgacag   2880

ccccaatgtg cacagagcag tggagagggc cgggcggccg gttgggagtt ggaggtgaag   2940

gccgcatggg ggacctgcac caagggcctg gggaccgcag aggcgcccgg gcggacctct   3000

ccgactttcg ccctccagac accaccgcca ccagccagca aacaccctcc gcctcagttt   3060

ctcccacccc caccgacccc tcccccaccc atccaggggg cggggccaga ggtcaaggct   3120

agtgggtggg attggggagg gagagaggtg tcgagcagtc cccttggaga gccctggttt   3180

tactgggccc ccggcttggg gcgccttcct tcccc                              3215


<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence:Primer for
      use in construction of porcine Oct4-beta-geo plasmid

<400> SEQUENCE: 25

tcaaagcgct aaaatgtgat ttgg                                             24


<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence:Primer for
      use in construction  of porcine Oct4-beta-geo plasmid

<400> SEQUENCE: 26

cgatctcgag ggatcccaga ccggggaact                                       30


<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence:Primer for
      use in construction of pPGK-beta-geo plasmid

<400> SEQUENCE: 27

agcgcacgtc tgccgcgctg tt                                               22


<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence:Primer for
      use in construction of pPGK-beta-geo plasmid

<400> SEQUENCE: 28

cctgtagcca gctttcatca ac                                               22


<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence:Primer for
      use in construction of porcine Oct4-EGFP plasmid

<400> SEQUENCE: 29

cagggtcttc gaagaggggt cca                                              23
```

-continued

```
<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence:Primer for
      use in construction of porcine Oct4-EGFP plasmid

<400> SEQUENCE: 30

gtcgaccagg gctctccaag ggga                                          24


<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Primer for
      use in analysis of porcine Oct4-EGFP plasmid

<400> SEQUENCE: 31

acttagcaca gacaccasga cct                                           23


<210> SEQ ID NO 32
<211> LENGTH: 378
<212> TYPE: DNA
<213> ORGANISM: Bacteriophage lambda

<400> SEQUENCE: 32

agccatgctg ggttgatcct cccacctggc tgtgcttcca agggcctcct gttgggtcag     60

ggatctggcg gggggctgct ggacccagag gtggggaggc ttctctcatg ccccccgccc    120

taggacttct gcggagggat ggcctactgt gcacctcagg tcagagaggg gctggtgccc    180

caaggcggcc tggagacccc tcagccctag ggccaggcag gagtcggggt ggggagcaac    240

tccgaggggg cctccctgga gccctatgcc acccccgttg gcactgcaca gctggacaag    300

gagaaactag agccgaatcc tgagaagtcc caggacatca aaacgcttca gaaagacctt    360

caacaatttg ccaagctt                                                  378


<210> SEQ ID NO 33
<211> LENGTH: 1248
<212> TYPE: DNA
<213> ORGANISM: Mus sp.

<400> SEQUENCE: 33

agtggatccc ccgggctgca ggaattccgg gatggatcct cgaacctggc taagcttcca     60

agggcctcca ggtgggcctg gaatcggacc aggctcagag gtattgggga tctccccatg    120

tccgcccgca tacgagttct gcggagggat ggcatactgt ggacctcagg ttggtctggg    180

cctagtcccc caagttggcg tggagacttt gcagcctgag ggccaggcag gagcacgagt    240

ggaaagcaac tcagagggaa cctcctctga gccctgtgcc gaccgcccca atgccgtgaa    300

gttggagaag gtggaaccaa ctcccgagga gtcccaggac atgaaagccc tgcagaagga    360

gctagaacag tttgccaagc tgctgaagca gaagaggatc accttggggt acacccaggc    420

cgacgtgggg ctcaccctgg gcgttctctt tggaaaggtg ttcagccaga ccaccatctg    480

tcgcttcgag gccttgcagc tcagccttaa gaacatgtgt aagctgcggc ccctgctgga    540

gaagtgggtg gaggaagccg acaacaatga caaccttcag gagatatgca aatcggagac    600

cctggtgcag gcccggaaga gaaagcgaac tagcattgag aaccgtgtga ggtggagtct    660

ggagaccatg tttctgaagt gcccgaagcc ctccctacag cagatcactc acatcgccaa    720
```

```
tcagcttggg ctagagaagg atgtggttcg agtatggttc tgtaaccggc gccagaaggg    780

caaaagatca agtattgagt attcccaacg agaagagtat gaggctacag ggacaccttt    840

cccagggggg gctgtatcct ttcctctgcc cccaggtccc cactttggca ccccaggcta    900

tggaagcccc cacttcacca cactctactc agtccctttt cctgagggcg aggcctttcc    960

ctctgttccc gtcactgctc tgggctctcc catgcattca aactgaggca ccagccctcc   1020

ctggggatgc tgtgagccaa ggcaagggag gtagacaaga gaacctggag ctttggggtt   1080

aaattctttt actgaggagg gattaaaagc acaacagggg tggggggtgg gatggggaaa   1140

gaagctcagt gatgctgttg atcaggagcc tggcctgtct gtcactcatc attttgttct   1200

taaataaaga ctgggacaca cagtaaaaaa aaaaaaaaaa aactcgag                1248
```

<210> SEQ ID NO 34
<211> LENGTH: 324
<212> TYPE: PRT
<213> ORGANISM: Mus sp.

<400> SEQUENCE: 34

```
Met Asp Pro Arg Thr Trp Leu Ser Phe Gln Gly Pro Pro Gly Gly Pro
  1               5                  10                  15

Gly Ile Gly Pro Gly Ser Glu Val Leu Gly Ile Ser Pro Cys Pro Pro
             20                  25                  30

Ala Tyr Glu Phe Cys Gly Gly Met Ala Tyr Cys Gly Pro Gln Val Gly
         35                  40                  45

Leu Gly Leu Val Pro Gln Val Gly Val Glu Thr Leu Gln Pro Glu Gly
     50                  55                  60

Gln Ala Gly Ala Arg Val Glu Ser Asn Ser Glu Gly Thr Ser Ser Glu
 65                  70                  75                  80

Pro Cys Ala Asp Arg Pro Asn Ala Val Lys Leu Glu Lys Val Glu Pro
                 85                  90                  95

Thr Pro Glu Glu Ser Gln Asp Met Lys Ala Leu Gln Lys Glu Leu Glu
            100                 105                 110

Gln Phe Ala Lys Leu Leu Lys Gln Lys Arg Ile Thr Leu Gly Tyr Thr
        115                 120                 125

Gln Ala Asp Val Gly Leu Thr Leu Gly Val Leu Phe Gly Lys Val Phe
    130                 135                 140

Ser Gln Thr Thr Ile Cys Arg Phe Glu Ala Leu Gln Leu Ser Leu Lys
145                 150                 155                 160

Asn Met Cys Lys Leu Arg Pro Leu Leu Glu Lys Trp Val Glu Glu Ala
                165                 170                 175

Asp Asn Asn Glu Asn Leu Gln Glu Ile Cys Lys Ser Glu Thr Leu Val
            180                 185                 190

Gln Ala Arg Lys Arg Lys Arg Thr Ser Ile Glu Asn Arg Val Arg Trp
        195                 200                 205

Ser Leu Glu Thr Met Phe Leu Lys Cys Pro Lys Pro Ser Leu Gln Gln
    210                 215                 220

Ile Thr His Ile Ala Asn Gln Leu Gly Leu Glu Lys Asp Val Val Arg
225                 230                 235                 240

Val Trp Phe Cys Asn Arg Arg Gln Lys Gly Lys Arg Ser Ser Ile Glu
                245                 250                 255

Tyr Ser Gln Arg Glu Glu Tyr Glu Ala Thr Gly Thr Pro Phe Pro Gly
            260                 265                 270

Gly Ala Val Ser Phe Pro Leu Pro Pro Gly Pro His Phe Gly Thr Pro
```

-continued

```
        275                 280                 285

Gly Tyr Gly Ser Pro His Phe Thr Thr Leu Tyr Ser Val Pro Phe Pro
    290                 295                 300

Glu Gly Glu Ala Phe Pro Ser Val Pro Val Thr Ala Leu Gly Ser Pro
305                 310                 315                 320

Met His Ser Asn


<210> SEQ ID NO 35
<211> LENGTH: 499
<212> TYPE: DNA
<213> ORGANISM: Homo sapiens

<400> SEQUENCE: 35

gaattcaaga ccagcctggg taacatagca aggccccatc tctactaaaa ataaaaaaac     60

taacagggca cagtggtcca agcctgtagt cccagccact taggaggctg gagcagaagg    120

attgctttgg cccagtagat cgaggctaca ttgagccatc attgtactcc actgcactcc    180

agtctgggca acaaagtgag accctgtctt aaaaaataaa aataaaaaaa gtttctgtgg    240

gggacctgca ctgaggtcct ggagggggcgc cagttgtgtc tcccggtttt ccccttccac    300

agacaccatt gccaccacca ttaggcaaac atgccttcgc ctcagtttct ccccccacct    360

ccctctcctc cacccatcca gggggcgggg ccagaggtca aggctagtgg gtgggactgg    420

ggagggagag aggggttgag tagtcccttc gcaagccctc atttcaccag gcccccggct    480

tggggcgcct tccttcccc                                                 499


<210> SEQ ID NO 36
<211> LENGTH: 550
<212> TYPE: DNA
<213> ORGANISM: Mus sp.

<400> SEQUENCE: 36

tgcaatggct gtcttgtcct ggccttggac atgggctgaa atactgggtt cacccatatc     60

taggactcta gacgggtggg taagcaagaa ctgaggagtg gccccagaaa taattggcac    120

acgaacattc aatggatgtt ttaggctctc cagaggatgg ctgagtgggc tgtaaggaca    180

ggccgagagg gtgcagtgcc aacaggcttt gtggtgcgat ggggcatccg agcaactggt    240

ttgtgaggtg tccggtgacc caaggcaggg gtgagaggac cttgaaggtt gaaaatgaag    300

gccttcctgg ggtcccgtcc taagggttgt cctgtccaga cgtccccaac ctccgtctgg    360

aagacacagg cagatagcgc tcgcctcagt ttctccaccc ccacagctct gctcctccac    420

ccacccaggg ggcggggcca gaggtcaagg ctagagggtg ggattgggga gggagaggtg    480

aaaccgtccc taggtgagcc gtctttccac caggccccccg gctcggggtg cccaccttcc    540

ccatggctgg                                                           550


<210> SEQ ID NO 37
<211> LENGTH: 739
<212> TYPE: DNA
<213> ORGANISM: Musca sp.

<400> SEQUENCE: 37

gagccactga ccctagccaa cagctcaggc gggctgggcc caggctcaga actctgtcct     60

ggctatgtac actgtggggt gctctgggct ttttgaggct gtgtgattca ccctggggcc    120

ttcgttcagg gcatggtgta ggagcagaca gacaaacacc atcccttgca gacaggcact    180

ctgagggcta ttctcttgca aagataacta agcaccaggc cagtaatggg atcctcagac    240
```

-continued

```
tgggcccaga aaaccactct aggaaagttc agggtaggct ctctgcaccc cctcctccta    300

atcccgtctc cttagtgtct ttccgccagc acaggaatgg gggaggggtg ggtgacgagg    360

atgaacaccg gagtccctgg aggaagggaa gcagggtatc tccatctgag gctctgtctt    420

tgaggagagg tggagagctg gggaagtctt gtgtgagggg attggggctc aggagggggt    480

tggggagcag gaagttgtcc ccaggggagc catcctggcc cattcaaggg ttgagtactt    540

gtttagggtt agagctgccc ctctggggac caggattgtc cagccaaggc cattgtcctg    600

ccccttccc ccagtccctc ccaggcccct ttgaacctga agtcagatat ttcttctctc    660

tacccacctc ccacccgttg ggtttctcca cccaggaact aggctggaag ctgggatgag    720

gaggtggggg agggagaac                                                 739


<210> SEQ ID NO 38
<211> LENGTH: 4
<212> TYPE: DNA
<213> ORGANISM: Artificial Sequence
<220> FEATURE:
<223> OTHER INFORMATION: Description of Artificial Sequence:
      Tetranucleotide found in many promoter sequences.

<400> SEQUENCE: 38

tata                                                                   4


<210> SEQ ID NO 39
<211> LENGTH: 26
<212> TYPE: DNA
<213> ORGANISM: Sus sp.

<400> SEQUENCE: 39

gggggcgggg ccagaggtca aggcta                                          26
```